United States Patent
Kobayashi et al.

(10) Patent No.: US 10,342,503 B2
(45) Date of Patent: Jul. 9, 2019

(54) MEDICAL IMAGE PROCESSING APPARATUS, X-RAY DIAGNOSTIC APPARATUS, AND X-RAY COMPUTED TOMOGRAPHY APPARATUS

(71) Applicant: TOSHIBA MEDICAL SYSTEMS CORPORATION, Otawara-shi (JP)

(72) Inventors: Yoshimasa Kobayashi, Nasushiobara (JP); Hisanori Kato, Otawara (JP); Shumpei Ohashi, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 634 days.

(21) Appl. No.: 14/475,824

(22) Filed: Sep. 3, 2014

(65) Prior Publication Data

US 2015/0063526 A1 Mar. 5, 2015

(30) Foreign Application Priority Data

Sep. 5, 2013 (JP) .................................. 2013-184508

(51) Int. Cl.
*A61B 6/00* (2006.01)
*A61B 6/03* (2006.01)
*G06T 11/00* (2006.01)

(52) U.S. Cl.
CPC ............ *A61B 6/5282* (2013.01); *A61B 6/032* (2013.01); *G06T 11/005* (2013.01); *A61B 6/487* (2013.01)

(58) Field of Classification Search
CPC ........................................................ G06T 5/50
See application file for complete search history.

(56) References Cited

U.S. PATENT DOCUMENTS

| | | | | | |
|---|---|---|---|---|---|
| 5,771,269 | A | * | 6/1998 | Chao | ........................ A61B 6/06 378/147 |
| 6,007,243 | A | * | 12/1999 | Ergun | .................... A61B 6/548 348/E5.081 |

(Continued)

FOREIGN PATENT DOCUMENTS

| JP | 02-244881 A | 9/1990 |
|---|---|---|
| JP | WO 2009/142166 | 11/2009 |
| JP | 2011-147615 | 8/2011 |

OTHER PUBLICATIONS

Steven R. Meikle, et al., "A Transmission-Dependent Method for Scatter Correction in SPECT", The Journal of Nuclear Medicine, vol. 35, No. 2, Feb. 1994, pp. 360-367.

(Continued)

*Primary Examiner* — David P Porta
*Assistant Examiner* — Djura Malevic
(74) *Attorney, Agent, or Firm* — Oblon, McClelland, Maier & Neustadt, L.L.P.

(57) ABSTRACT

An X-ray image processing apparatus includes a storage unit, a transformed image generation unit, a scattered ray image generation unit, and a scattered ray reduced image generation unit. The storage unit stores a medical image. The transformed image generation unit generates a transformed image by transforming pixel values, of a plurality of pixel values constituting the medical image, which are higher than a reference value obtained based on a representative value of the plurality of pixel values into pixel values lower than the reference value. The scattered ray image generation unit generates a scattered ray image based on the transformed image and a scattering function. The scattered ray reduced image generation unit generates a scattered ray reduced image with reduced scattered rays by using the medical image and the scattered ray image.

9 Claims, 14 Drawing Sheets

(56) References Cited

U.S. PATENT DOCUMENTS

| | | | | |
|---|---|---|---|---|
| 6,018,565 A * | 1/2000 | Ergun | | A61B 6/4405 348/E5.081 |
| 6,215,846 B1 * | 4/2001 | Mazess | | A61B 6/4225 348/E3.045 |
| 6,282,261 B1 * | 8/2001 | Mazess | | A61B 6/4225 348/E3.045 |
| 6,298,109 B1 * | 10/2001 | Ergun | | A61B 6/4405 348/E5.081 |
| 6,315,445 B1 * | 11/2001 | Mazess | | A61B 6/4225 348/E3.045 |
| 7,031,427 B2 * | 4/2006 | Dinten | | A61B 6/5282 378/18 |
| 7,496,171 B2 * | 2/2009 | Rinkel | | G01T 1/29 378/207 |
| 7,756,316 B2 * | 7/2010 | Odry | | G06K 9/4638 382/131 |
| 8,063,957 B2 * | 11/2011 | Goma | | H04N 5/367 348/229.1 |
| 8,625,740 B2 * | 1/2014 | Harding | | G01N 23/20 378/207 |
| 8,837,771 B2 * | 9/2014 | Lay | | G06K 9/34 378/4 |
| 8,913,711 B2 * | 12/2014 | Moriyasu | | A61B 6/03 378/4 |
| 9,655,587 B2 * | 5/2017 | Butzine | | A61B 6/544 |
| 9,750,477 B2 * | 9/2017 | Kitagawa | | A61B 6/542 |
| 9,886,765 B2 * | 2/2018 | Naito | | A61B 6/4291 |
| 2002/0012477 A1 * | 1/2002 | Inoue | | G06T 5/20 382/284 |
| 2003/0016854 A1 * | 1/2003 | Inoue | | G06T 5/10 382/132 |
| 2003/0016855 A1 * | 1/2003 | Shinbata | | G06T 5/009 382/132 |
| 2003/0190067 A1 * | 10/2003 | Tsujii | | A61B 6/5217 382/132 |
| 2005/0078787 A1 * | 4/2005 | Dinten | | A61B 6/5282 378/54 |
| 2008/0027316 A1 * | 1/2008 | Baumgart | | A61B 6/463 600/425 |
| 2009/0003698 A1 * | 1/2009 | Milward | | G06K 9/38 382/171 |
| 2010/0080433 A1 * | 4/2010 | Noshi | | G06T 11/005 382/131 |
| 2010/0157041 A1 * | 6/2010 | Klaiman | | A61B 5/0044 348/77 |
| 2010/0172474 A1 * | 7/2010 | Vogt | | G06T 5/50 378/98.12 |
| 2011/0122138 A1 * | 5/2011 | Schmidt | | G06K 9/6253 345/440 |
| 2011/0268328 A1 * | 11/2011 | Bar-Aviv | | G06T 5/50 382/128 |
| 2012/0148156 A1 * | 6/2012 | Sehnert | | A61B 6/4291 382/171 |
| 2012/0179425 A1 * | 7/2012 | Zhang | | G02B 27/0075 702/189 |
| 2012/0207370 A1 * | 8/2012 | Fahimian | | A61B 6/032 382/131 |
| 2012/0288173 A1 * | 11/2012 | Rai | | G06K 9/46 382/131 |
| 2012/0289825 A1 * | 11/2012 | Rai | | A61B 6/12 600/425 |
| 2012/0300904 A1 * | 11/2012 | Shimada | | A61B 6/4291 378/62 |
| 2013/0094739 A1 * | 4/2013 | Okabe | | A61B 6/032 382/131 |
| 2013/0156158 A1 * | 6/2013 | Noji | | A61B 5/08 378/62 |
| 2013/0202177 A1 * | 8/2013 | Bar-Aviv | | G06T 11/008 382/131 |
| 2013/0204134 A1 * | 8/2013 | Harks | | A61B 5/0084 600/439 |
| 2013/0223587 A1 * | 8/2013 | Moriyasu | | A61B 6/03 378/5 |
| 2013/0331725 A1 * | 12/2013 | Noji | | A61B 6/5217 600/534 |
| 2014/0056407 A1 * | 2/2014 | Goldammer | | A61B 6/4035 378/62 |
| 2014/0198895 A1 * | 7/2014 | Hoshino | | A61B 6/482 378/36 |

OTHER PUBLICATIONS

Office Action dated Apr. 24, 2018, in Japanese Patent Application No. 2017-130379.

\* cited by examiner

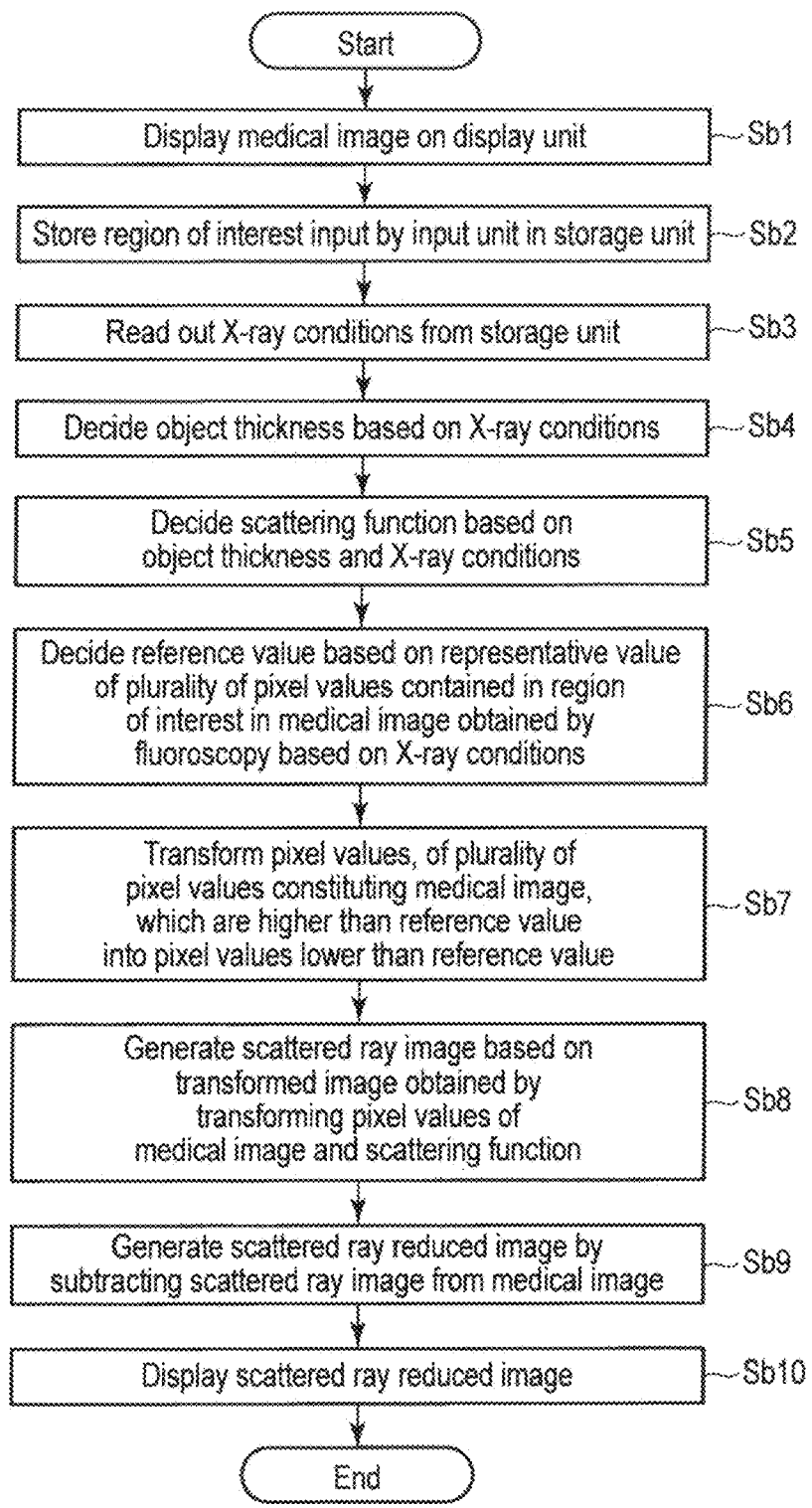
F I G. 7

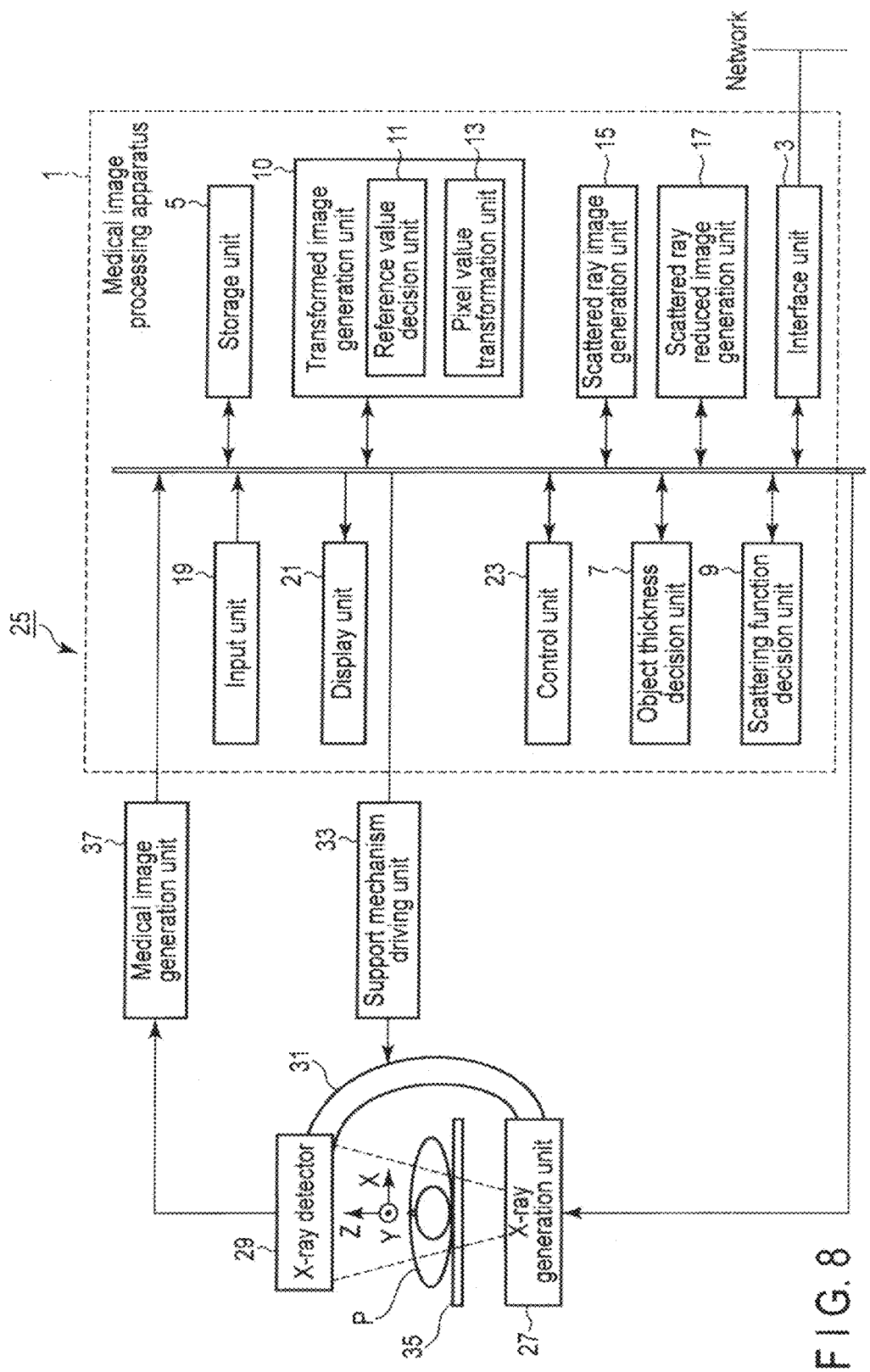
F I G. 8

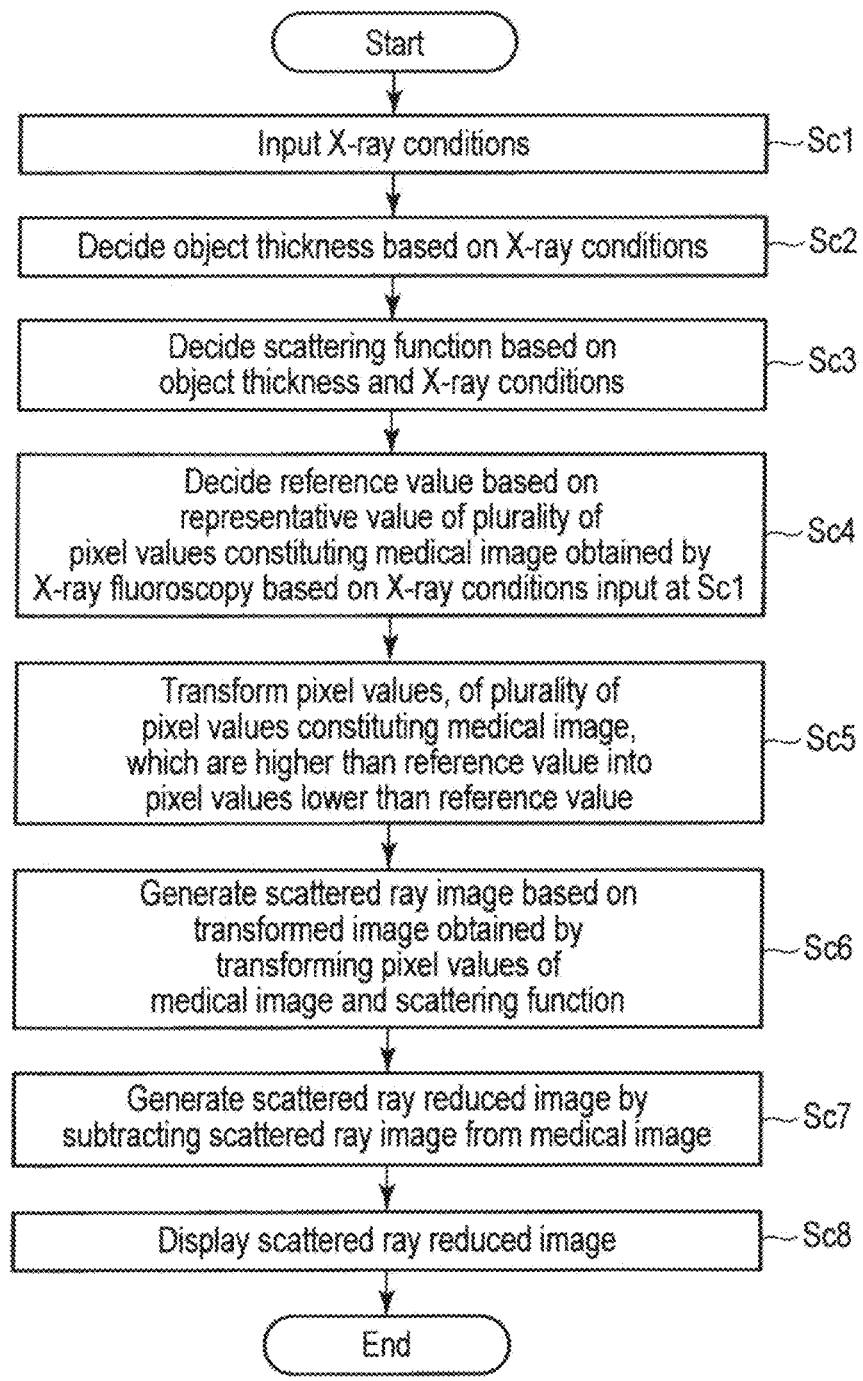
F I G. 9

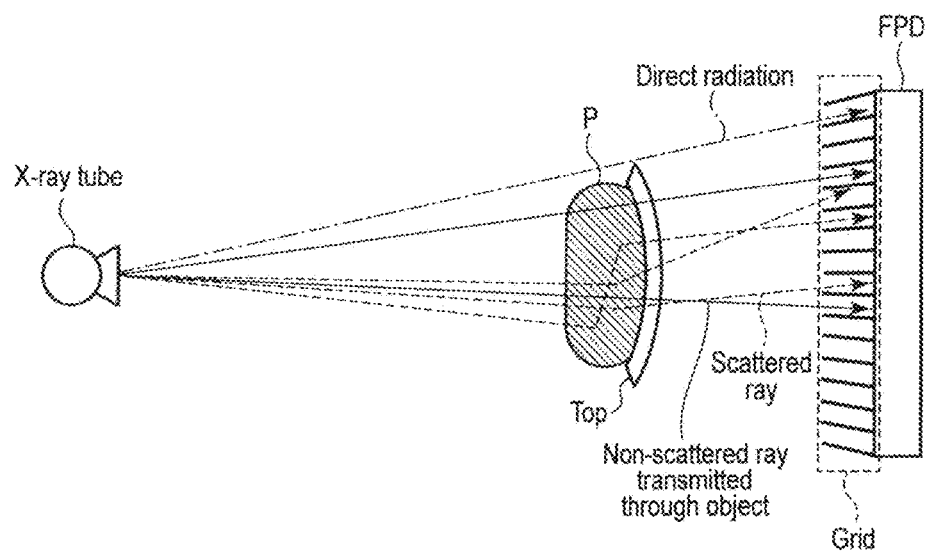
F I G. 14

MEDICAL IMAGE PROCESSING APPARATUS, X-RAY DIAGNOSTIC APPARATUS, AND X-RAY COMPUTED TOMOGRAPHY APPARATUS

CROSS-REFERENCE TO RELATED APPLICATIONS

This application is based upon and claims the benefit of priority from the prior Japanese Patent Application No. 2013-184508, filed Sep. 5, 2013 the entire contents of which are incorporated herein by reference.

FIELD

Embodiments described herein relate generally to a medical image processing apparatus, an X-ray diagnostic apparatus, and X-ray computed tomography apparatus.

BACKGROUND

When detecting X-rays by using an X-ray fluoroscopic apparatus, X-rays (to be referred to as scattered rays hereinafter) scattered by an object sometimes enter the detector. A grid is used to prevent scattered rays from entering the detector. FIG. 14 shows how an FPD (Flat Panel Detector) detects X-rays generated from an X-ray tube. The direct radiation indicated by the one-dot dashed line is an X-ray which is not transmitted through an object P. The scattered rays indicated by the dotted lines are transmitted through the object P and scattered by the object P in the process of being transmitted. The unscattered rays indicated by the solid lines, which are transmitted through the object P, are X-rays which are transmitted through the object P without being scattered.

The grid has a pattern structure in which aluminum foils or the like through which X-rays are transmitted and lead foils or the like which absorb scattered X-rays are alternately arranged. As shown in FIG. 14, when X-ray imaging or X-ray fluoroscopy is executed while the grid is placed on the X-ray incident surface of the detector, the grid removes scattered rays. This makes it difficult for scattered rays to reach the detector. This reduces the dose of scattered rays reaching the detector. However, some scattered rays reach the detector without being removed. The scattered rays having reached the detector are displayed as noise on an image (to be referred to as a medical image hereinafter) generated based on an output from the detector. For this reason, a medical image is processed to reduce scattered ray components on the image (this operation will be referred to as scattered ray correction processing hereinafter).

Conventionally, as one type of scattered ray correction processing, there is available a technique of executing scattered ray correction processing in computation in a frequency space. The Fourier transform of an image (to be referred to as a scattered ray reduced image hereinafter) having undergone a reduction in scattered ray component by scattered ray correction processing is performed based on the Fourier transform of a medical image and the Fourier transform of a scattering function. A scattered ray reduced image is generated by applying an inverse Fourier transform to the Fourier transform of the scattered ray reduced image. With the above method, however, it is not possible to change a scattering function in accordance with the position of each pixel in a medical image. It is therefore not possible to properly reduce scattered ray components in, for example, a medical image containing direct radiation components or a medical image or the like having non-direct radiation components which are transmitted through a partially thin portion (to be referred to as a small body thickness portion hereinafter) of an object P. For example, this raises a problem that scattered ray components are excessively corrected (this operation will be referred to as excessive correction hereinafter).

In order to solve the above problem, there is available a method of generating a scattered ray reduced image by executing a repetitive operation a plurality of times to be described below. In this method, when the repeat count is 1, the first scattered ray components are estimated based on a medical image. In this case, the first scattered ray components are calculated by multiplying the convolution sum of a plurality of pixel values in the medical image and a scattering function by a direct radiation ratio. The direct radiation ratio is the ratio of the dose of direct radiation to the sum of the dose of direct radiation and the dose of scattered rays at each pixel in the medical image. The first scattered ray reduced image is then generated by subtracting the first scattered ray components from the medical image.

When the repeat count is 2, the second scattered ray components are estimated based on the first scattered ray reduced image. In this case, the second scattered ray components are calculated by multiplying the convolution sum of a plurality of pixel values in the first scattered ray reduced image and a scattering function by a direct radiation ratio. The direct radiation ratio is the ratio of the dose of direct radiation to the sum of the dose of direct radiation and the dose of scattered rays at each pixel in the first scattered ray reduced image. The second scattered ray reduced image is then generated by subtracting the first scattered ray components from the second scattered ray components.

When the repeat count is n (n is a natural number equal to or more than 2), the nth scattered ray components are estimated based on the (n−1)th scattered ray reduced image. In this case, the nth scattered ray components are calculated by multiplying the convolution sum of a plurality of pixel values in the (n−1)th scattered ray reduced image and a scattering function by a direct radiation ratio. The direct radiation ratio is the ratio of the dose of direct radiation to the sum of the dose of direct radiation and the dose of scattered rays at each pixel in the (n−1)th scattered ray reduced image. The nth scattered ray reduced image is then generated by subtracting the (n−1)th scattered ray components from the nth scattered ray components. A scattered ray reduced image is generated by repeating the above processing a predetermined number of times.

In general, the larger the repeat count n, the higher the accuracy of scattered ray correction processing. According to the above technique, however, as the value of n increases, the number of times of convolution sum calculation increases. This leads to an increase in calculation amount. That is, the above technique has a problem that it takes much time to execute scattered ray correction processing. For example, in X-ray fluoroscopy, display delay or frame drop occurs, resulting in a difficulty in real-time display.

It is an object to provide a medical image processing apparatus, an X-ray diagnostic apparatus, and an X-ray computed tomography apparatus which can generate scattered ray reduced images without excessive correction, while suppressing a calculation amount, from a medical image having direct radiation components and even from a medical image having non-direct radiation components transmitted through a partially thin portion of an object.

BRIEF DESCRIPTION OF THE DRAWINGS

FIG. 7 is a flowchart showing an example of a procedure for scattered ray correction processing according to a modification of the first embodiment;

FIG. 8 is a block diagram showing an example of the arrangement of an X-ray diagnostic apparatus according to the second embodiment;

FIG. 9 is a flowchart showing an example of a procedure for scattered ray correction processing according to the second embodiment

FIG. 14 is a view concerning a related art.

DETAILED DESCRIPTION

Figure 1:
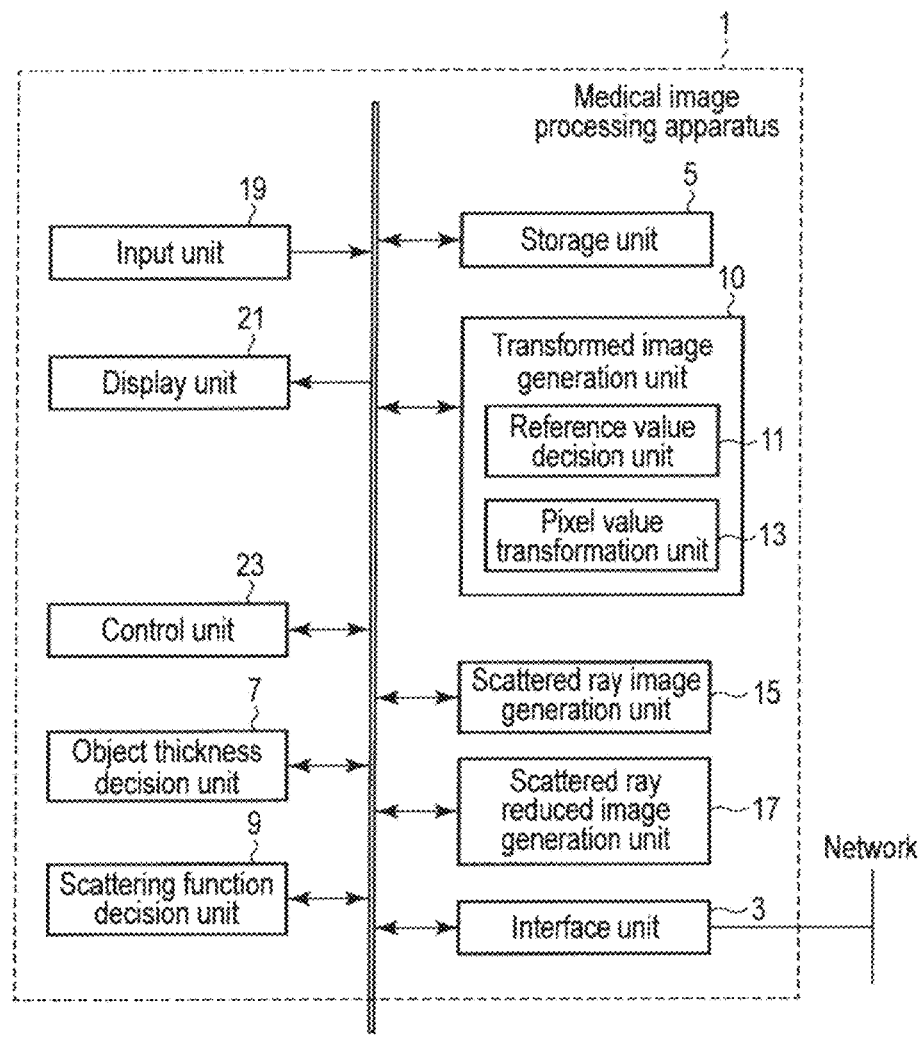
FIG. 1 is a block diagram showing an example of the arrangement of a medical image processing apparatus according to the first embodiment.

An X-ray image processing apparatus according to this embodiment includes a storage unit, a transformed image generation unit, a scattered ray image generation unit, and a scattered ray reduced image generation unit. The storage unit stores a medical image. The transformed image generation unit generates a transformed image by transforming pixel values, of a plurality of pixel values constituting the medical image, which are higher than a reference value obtained based on a representative value of the plurality of pixel values into pixel values lower than the reference value. The scattered ray image generation unit generates a scattered ray image based on the transformed image and a scattering function. The scattered ray reduced image generation unit generates a scattered ray reduced image with reduced scattered rays by using the medical image and the scattered ray image.

A medical image processing apparatus 1 according to an embodiment will be described below with reference to the accompanying drawings. Note that the same reference numerals denote constituent elements having almost the same functions and arrangements in the following description, and a repetitive description will be made only when required.

First Embodiment

FIG. 1 shows the arrangement of the medical image processing apparatus 1 according to the first embodiment. The medical image processing apparatus 1 includes an interface unit 3, a storage unit 5, an object thickness decision unit 7, a scattering function decision unit 9, a transformed image generation unit 10, a scattered ray image generation unit 15, a scattered ray reduced image generation unit 17, an input unit 19, a display unit 21, and a control unit 23.

The interface unit 3 is connected to a plurality of medical image diagnostic apparatuses via a network. The medical image diagnostic apparatuses include, for example, an X-ray diagnostic apparatus, X-ray CT (Computed Tomography) apparatus, MRI (Magnetic Resonance Imaging) apparatus, ultrasonic diagnostic apparatus, nuclear medicine diagnostic apparatus (for example, PET (Positron Emission Computed Tomography) apparatus), and SPECT (Single Photon Emission Computed Tomography) apparatus.

The interface unit 3 outputs the medical image and X-ray conditions acquired from the medical image diagnostic apparatus to the storage unit 5. The X-ray conditions include conditions at the time of X-ray imaging or X-ray fluoroscopy, such as a tube voltage, a tube current, a pulse time, and an irradiation field indicating the irradiation range of X-rays. Note that the interface unit 3 may output the medical image acquired from the medical image diagnostic apparatus to the transformed image generation unit 10, the scattered ray reduced image generation unit 17, the display unit 21, and the like, as needed.

The storage unit 5 stores the X-ray conditions and medical image acquired from the interface unit 3 and instructions and the like from the operator which are sent from the input unit 19. Note that the operator can change the X-ray conditions, as needed, via the input unit 19. The instructions from the operator include various types of instructions, commands, information, selections, and settings which are input by the operator via the input unit 19. Note that the storage unit 5 may store a program associated with scattered ray correction processing (to be described later).

The object thickness decision unit 7 decides an object thickness based on the X-ray conditions stored in the storage unit 5. The X-ray conditions are conditions associated with the generation of X-rays, such as a tube voltage, tube current, and imaging time. The object thickness decision unit 7 includes a memory (not shown) and stores a correspondence table (to be referred to as a tube voltage/object thickness correspondence table hereinafter) between tube voltages and object thicknesses. Note that the tube voltage/object thickness correspondence table may be a correspondence table of object thicknesses with respect to elements (e.g., tube currents or tube current time products) other than tube voltages. More specifically, the object thickness decision unit 7 decides an object thickness based on the X-ray conditions and tube voltage/object thickness correspondence table read out from the storage unit 5. Note that an object thickness may be decided by an instruction issued by the operator via the input unit 19.

The scattering function decision unit 9 decides a scattering function based on the X-ray conditions stored in the storage unit 5 and the object thickness decided by the object thickness decision unit 7. The scattering function decision unit 9 includes a memory (not shown) and stores a correspondence table (to be referred to as a scattering function correspondence table hereinafter) of scattering functions with respect to X-ray conditions and object thicknesses. Note that a scattering function is a function corresponding to scattered ray components in a medical image. More specifically, the scattering function decision unit 9 decides a scattering function based on the object thickness decided by the object thickness decision unit 7, the X-ray conditions read out from the storage unit 5, and the scattering function correspondence table.

The transformed image generation unit 10 generates a transformed image by transforming pixel values, of a plurality of pixel values constituting a medical image, which are higher than the reference value obtained based on the representative value of a plurality of pixel values into pixel values lower than the reference value. The transformed image generation unit 10 includes a reference value decision unit 11 and a pixel value transformation unit 13.

The reference value decision unit 11 decides a reference value based on the representative value of a plurality of pixel values constituting a medical image. More specifically, the reference value decision unit 11 decides a reference value by multiplying the representative value of the plurality of pixel values constituting the medical image by a predetermined constant. The reference value decision unit 11 includes a memory (not shown) and stores a predetermined constant. Note that the predetermined constant may be changed in accordance with an instruction issued by the operator via the input unit 19. The predetermined constant will be described in detail later. The reference value decision unit 11 decides the mode value of the plurality of pixel values constituting the medical image, and uses the mode value as the above representative value.

Note that when performing X-ray fluoroscopy or continuous X-ray imaging, the object thickness decision unit 7, the scattering function decision unit 9, and the reference value decision unit 11 may execute processing before X-ray fluoroscopy or continuous X-ray imaging. A medical image used for each process described above is acquired via the interface unit 3 before X-ray fluoroscopy or continuous X-ray imaging.

Figure 2:
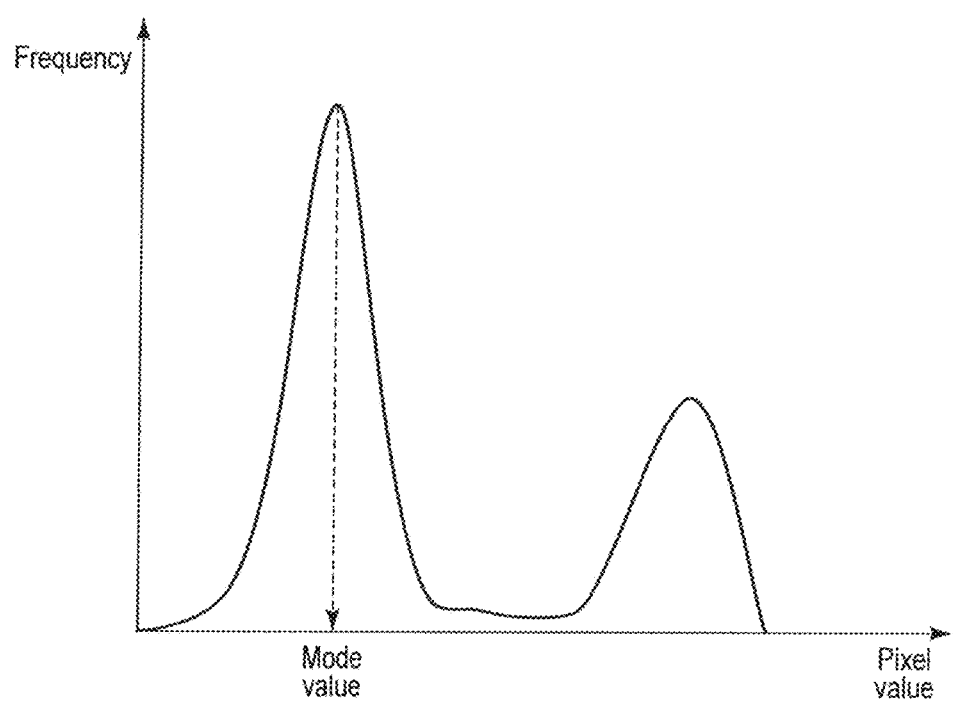
FIG. 2 is a graph showing an example of the distribution of a plurality of pixel values constituting a medical image according to the first embodiment.

FIG. 2 is a graph showing an example of the distribution (pixel value distribution) of a plurality of pixels constituting a medical image. In the pixel value distribution, direct radiation components exist in the range of pixel values higher than non-direct radiation components because the dose is less attenuated by the transmittance of radiation through the object.

In addition, non-direct radiation components transmitted through a partially thin portion (to be referred to as a small body thickness portion hereinafter) of the object exist in the range of pixel values higher than non-direct radiation components because the dose is less attenuated by the transmittance of radiation through the object like direct radiation components. For a more concrete description, the following will be described by using a medical image aiming at a chest region. In a medical image aiming at a chest region, the thickness of the chest region is almost constant. However, a boundary portion between the object and the background or an arm or neck portion is sometimes projected on the medical image. The above portion is thinner than a central portion of the chest region, and hence the attenuation of the dose caused by the transmittance of radiation through the object is smaller than that of other non-direct radiation components. Therefore, non-direct radiation components transmitted through the small body thickness portion exist in the range of pixel values higher than those of other non-direct radiation components.

For the sake of simplicity, a medical image having direct radiation components will be described below. The same effects are provided with respect to a medical image having non-direct radiation components transmitted through a small body thickness portion.

The pixel value transformation unit 13 includes a memory (not shown) and stores a pixel value transformation table. The pixel value transformation table represents the correspondence relationship between pixel values before transformation and pixel values after transformation. The pixel value transformation unit 13 transforms pixel values, of a plurality of pixel values constituting a medical image, which are higher than a reference value into pixel values lower than the reference value, based on the pixel value transformation table and the reference value. For example, the pixel value transformation unit 13 transforms the pixel values of pixels having direct radiation components in a medical image into low pixel values.

More specifically, the pixel value transformation table represents the correspondence relationship between pixel values before transformation and pixel values after transformation to be described, for example, below. The pixel value transformation unit 13 executes identity transformation for pixel values, of the pixel values of a medical image, which are equal to or less than a reference value. Note that the pixel value transformation unit 13 may make invariable pixel values, of the pixel values of a medical image, which are equal to or less than a reference value. The pixel value transformation unit 13 transforms pixel values, of the pixel values of a medical image, which are equal to or more than a reference value and equal to or less than twice the reference value into pixel values equal to or less than the reference value. The pixel value transformation unit 13 transforms pixel values, of the pixel values of the medical image, which are equal to or more than twice the reference value into 0. Note that it is possible to reduce artifacts in the scattered ray image generated by the scattered ray image generation unit 15 by using the image generated by transforming the pixel values equal to or more than the reference value and equal to more than twice the reference value into low pixel values.

For the sake of a concrete description, the following description will use the pixel value transformation table having the above correspondence relationship as an example.

Note that the input unit 19 changes the pixel value transformation table by changing the reference value in accordance with an instruction from the operator or the like. The reference value is changed by changing the predetermined constant. The predetermined constant will be described in detail later.

The scattered ray image generation unit 15 generates a scattered ray image based on the scattering function and the transformed image obtained by transforming the plurality of pixel values constituting the medical image using the pixel value transformation unit 13. The scattered ray image is an image obtained by approximately changing the scattering function in accordance with the position of each pixel of the medical image. More specifically, the scattered ray image generation unit 15 generates the Fourier transform of the transformed image. The scattered ray image generation unit 15 generates the Fourier transform of the scattering function. The scattered ray image generation unit 15 divides the Fourier transform of the scattering function by the sum of the Fourier transform of the scattering function and 1 (the division result will be referred to as a scattering function term hereinafter). The scattered ray image generation unit 15 thereby generates the Fourier transform of the scattered ray image by multiplying the Fourier transform of the transformed image by the scattering function term.

The scattered ray image generation unit 15 generates a scattered ray image by applying an inverse Fourier transform to the Fourier transform of the scattered ray image. Multiplying the Fourier transform of a transformed image and a scattering function term corresponds to approximately changing the scattering function in accordance with the position of each pixel of the medical image in a real space.

Figure 3:
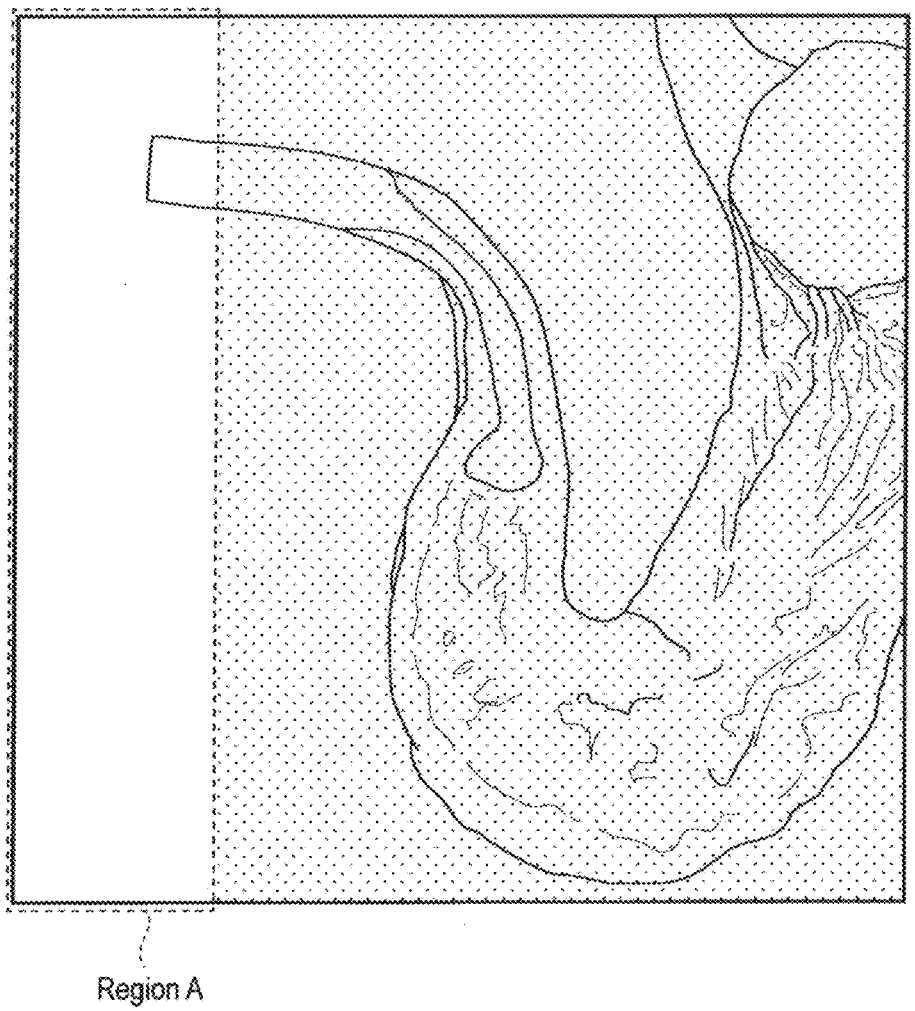
FIG. 3 is a view showing an example of a scattered ray reduced image generated by applying scattered ray correction processing to a medical image having direct radiation components according to the first embodiment.
Figure 4:
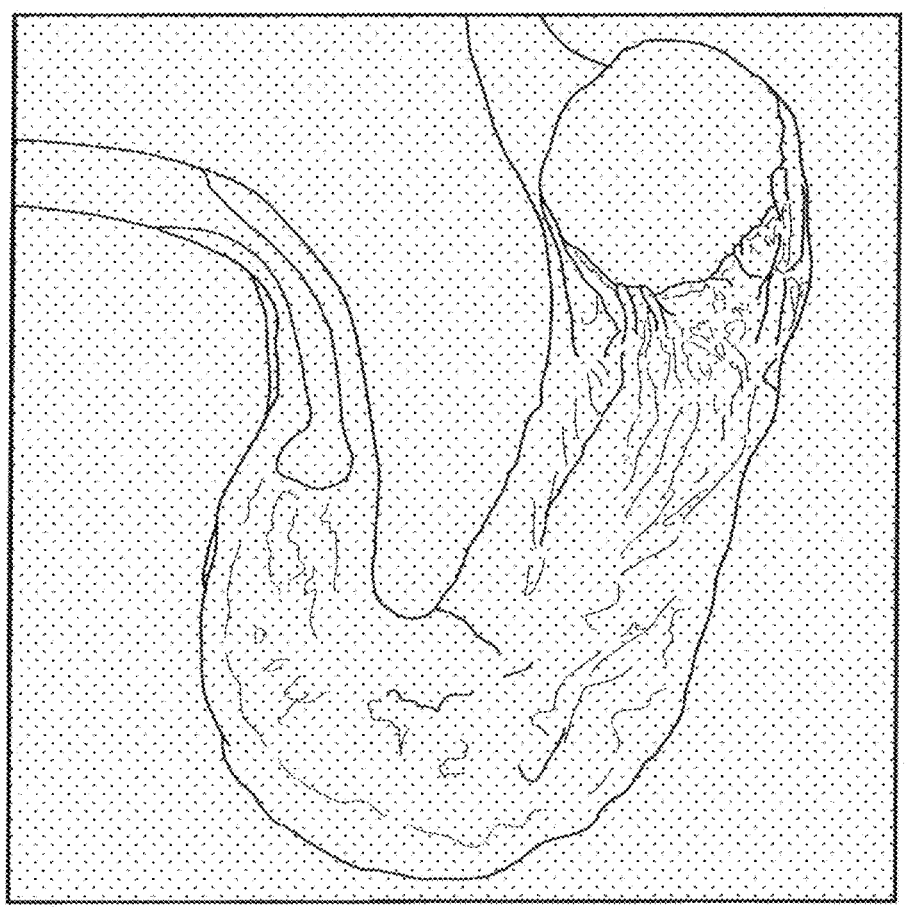
FIG. 4 is a view showing an example of a scattered ray reduced image generated by applying scattered ray correction processing to a medical image having no direct radiation component according to the first embodiment.

The scattered ray reduced image generation unit 17 generates a scattered ray reduced image by subtracting a scattered ray image from a medical image. The scattered ray image generation unit 15 outputs the scattered ray reduced image to the display unit 21. FIG. 3 is a view showing an example of a scattered ray reduced image of a medical image having direct radiation components. The region A in FIG. 3 is a pixel region containing many direct radiation components. The dot hatching in FIG. 3 indicates weak residual noise components. As is obvious from FIG. 3, scattered ray correction processing is properly executed without excessively correcting a medical image having direct radiation components (to be referred to as excessive correction hereinafter) by applying scattered ray correction processing in this embodiment to the medical image. FIG. 4 is a view showing an example of a scattered ray reduced image of a medical image having no direct radiation component. The dot hatching in FIG. 4 indicates weak residual noise components. As is obvious from FIG. 4, scattered ray correction processing is properly executed without excessive correction by applying scattered ray correction processing in the embodiment to a medical image having no direct radiation component.

The input unit 19 inputs various types of instructions, commands, information, selections, settings, and the like from the operator and the like to the control unit 23 (to be described later). Note that the input unit 19 may input a predetermined constant to the control unit 23 in accordance with an instruction from the operator. Based on this input, the control unit 23 updates a predetermined constant stored in the memory of the reference value decision unit 11. The predetermined constant is desired to be a value that transforms the pixel values of direct radiation components into low pixel values.

The input unit 19 includes input devices such as a trackball, switch buttons, mouse, mouse wheel, and keyboard for inputting various types of instructions, commands, information, selections, settings, and the like. Note that the input device may be a touch panel covering the display screen of the display unit 21. The input unit 19 can input a region of interest on a medical image which is used by the reference value decision unit 11. For example, the operator sets a region of interest by, for example, clicking and dragging the cursor of the mouse on the medical image displayed on the display unit 21.

The display unit 21 displays the scattered ray reduced image generated by the scattered ray reduced image generation unit 17. The display unit 21 can also display a medical image.

The control unit 23 includes a CPU (Central Processing Unit) and a memory (neither of which is shown). The control unit 23 temporarily stores, in a memory, information such as an instruction from the operator which is sent from the input unit 19. The control unit 23 comprehensively controls the object thickness decision unit 7, the scattering function decision unit 9, the transformed image generation unit 10, the scattered ray image generation unit 15, and the scattered ray reduced image generation unit 17 to execute image processing in accordance with instructions from the operator which are stored in the memory.

Figure 5:
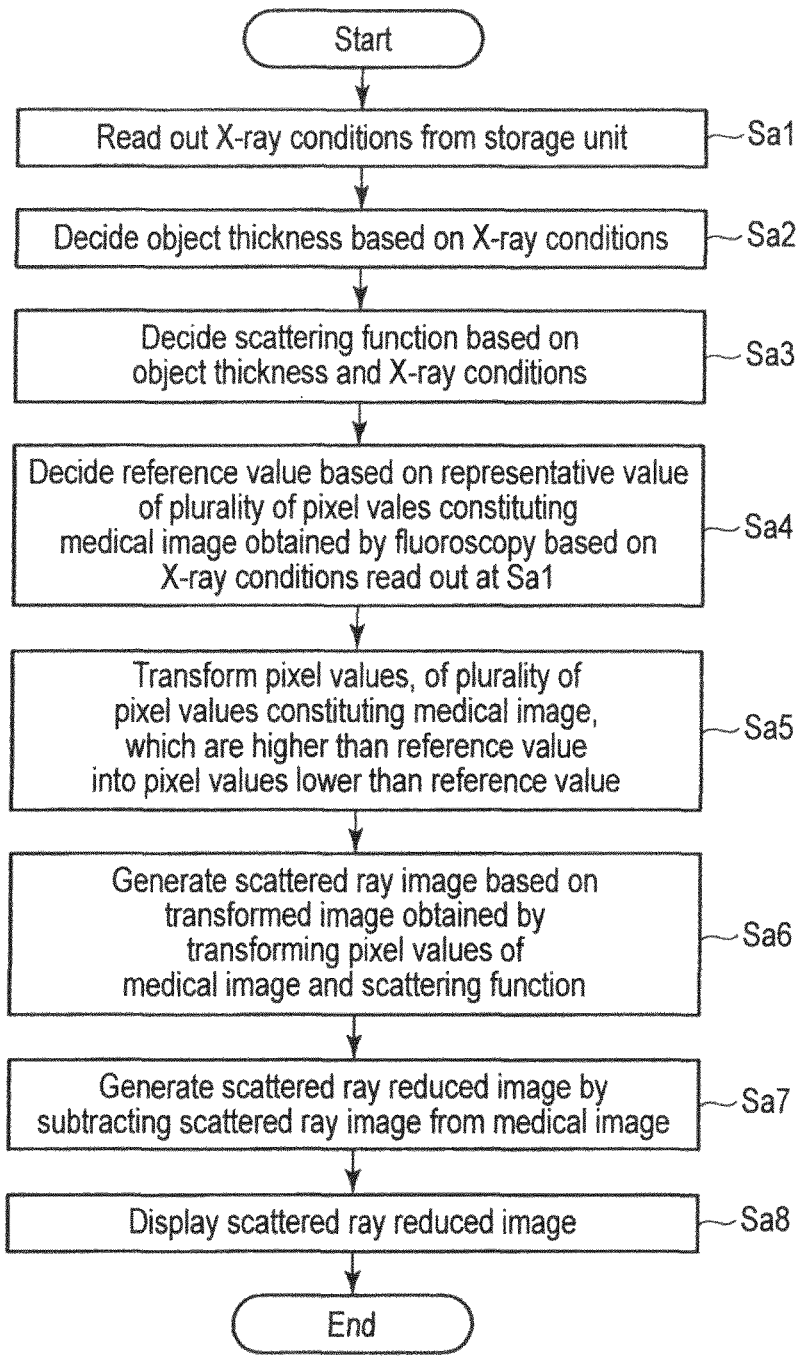
FIG. 5 is a flowchart showing an example of a procedure for scattered ray correction processing according to the first embodiment.

FIG. 5 is a flowchart showing an example of a procedure for scattered ray correction processing according to the first embodiment.

First of all, X-ray conditions are read out from the storage unit 5 (step Sa1). An object thickness is decided based on the readout X-ray conditions (step Sa2). A scattering function is decided based on the decided object thickness and the X-ray conditions read out in step Sa1 (step Sa3). A reference value is decided based on the representative value of a plurality of pixel values constituting a medical image obtained by X-ray imaging or X-ray fluoroscopy under the X-ray conditions read out in step Sa1 (step Sa4). Pixel values, of a plurality of pixel values constituting the medical image, which are higher than the reference value are transformed into pixel values lower than the reference value (step Sa5). A scattered ray image is generated based on the transformed image obtained by transforming the pixel values of the medical image and the scattering function (step Sa6). A scattered ray reduced image is generated by subtracting the scattered ray image from the medical image (step Sa7). The scattered ray reduced image is displayed (step Sa8).

(Modification)

A difference from the first embodiment is that the reference value decision unit 11 decides a reference value based on the representative value of the pixel values contained in a region of interest.

Figure 6:
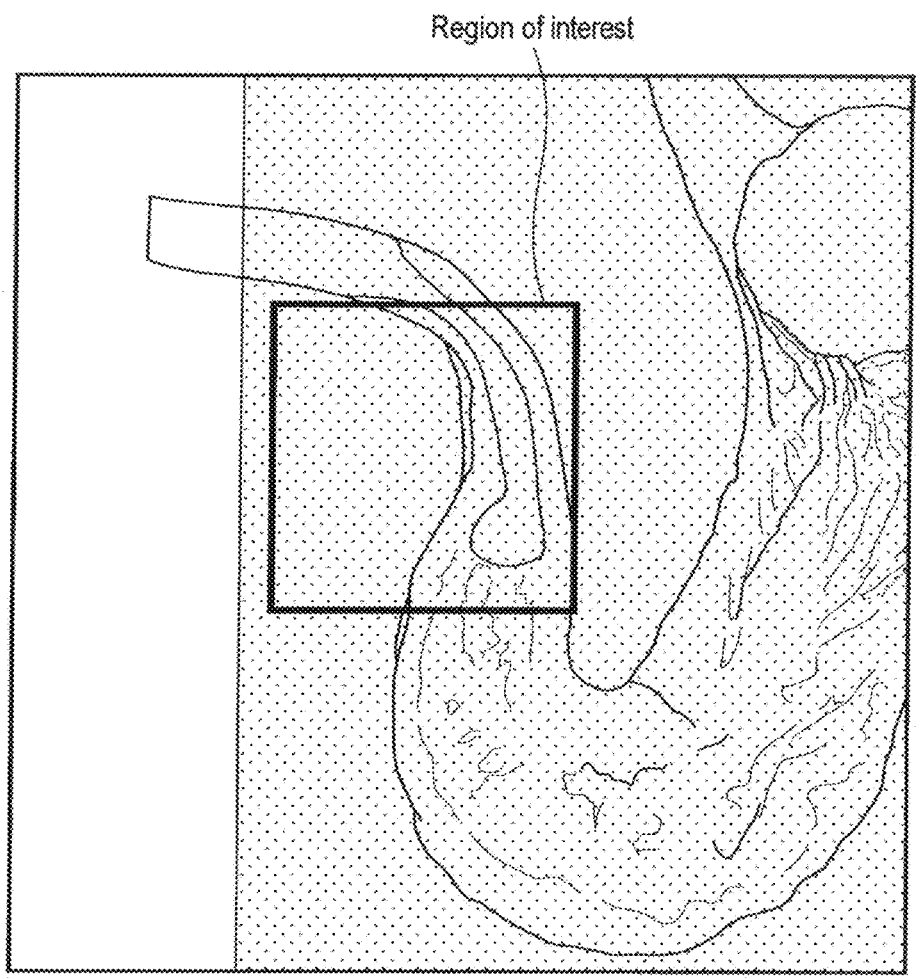
FIG. 6 is a view showing an example of setting a region of interest in a medical image according to a modification of the first embodiment.

The input unit 19 inputs the setting of a region of interest from the operator to the control unit 23. FIG. 6 is a view showing an example of the setting of a region on interest on a medical image. The reference value decision unit 11 decides a reference value by using, as the representative value, the average value or median value of a plurality of pixel values contained in the region of interest input from the input unit 19.

FIG. 7 is a flowchart showing an example of a procedure for scattered ray correction processing in a modification of the first embodiment.

The display unit 21 displays a medical image (step Sb1). The region of interest input via the input unit 19 is stored in the storage unit 5 (step Sb2). X-ray conditions are read out from the storage unit 5 (step Sb3). An object thickness is decided based on the readout X-ray conditions (step Sb4). A scattering function is decided based on the decided object thickness and the X-ray conditions read out in step Sb3 (step Sb5). A reference value is decided based on the representative value of a plurality of pixel values contained in the region of interest on the medical image obtained by X-ray imaging or X-ray fluoroscopy under the X-ray conditions read out in step Sb3 (step Sb6). Pixel values, of the plurality of pixel values constituting the medical image, which are higher than the reference value are transformed into pixel values lower than the reference value (step Sb7). A scattered ray image is generated based on the transformed image obtained by transforming the pixel values of the medical image and the scattering function (step Sb8). A scattered ray reduced image is generated by subtracting the scattered ray image from the medical image (step Sb9). The scattered ray reduced image is displayed (step Sb10).

According to the above arrangement, the following effects can be obtained.

The medical image processing apparatus 1 according to the first embodiment can decide a reference value based on a medical image. The apparatus can generate a transformed image by transforming the pixel value of each of a plurality of pixels constituting the medical image based on the pixel value transformation table and the reference value. The transformed image is obtained by transforming pixel values, of the plurality of pixel values constituting the medical image, which are higher than the reference value into pixel values lower than the reference value. In addition, it is possible to determine a scattering function based on X-ray conditions and an object thickness. According to the embodiment, it is possible to generate a scattered ray image by changing a scattering function in accordance with the position of each pixel of the medical image by using the transformed image. A scattered ray image is generated by reducing direct radiation components in the medical image. That is, it is possible to generate a scattered ray reduced image without excessive correction by applying scattered ray correction processing in this embodiment to a medical image having direct radiation components.

The same effects as those with respect to direct radiation components are provided with respect to non-direct radiation components transmitted through a small body thickness portion. A transformed image is obtained by transforming pixel values, of a plurality of pixel values constituting a medical image, which are higher than the reference value into pixel values lower than the reference value. Therefore, the scattered ray image generated based on the above transformed image and the scattering function is the one generated by reducing non-direct radiation components transmitted through a small body thickness portion of the medical image. That is, it is possible to generate a scattered ray reduced image without excessive correction by applying scattered ray correction processing in this embodiment to a medical image having a small body thickness portion.

In addition, according to the modification of the first embodiment, it is possible to decide a reference value based on a region of interest on an input medical image. A reference value includes, for example, the median value or average value of a plurality of pixel values contained in the region of interest. A transformed image can be generated by transforming the pixel value of each of a plurality of pixels constituting the medical image based on the decided reference value. That is, it is possible to generate a scattered ray reduced image without excessive correction by applying scattered ray correction processing in this embodiment to a medical image on which a region of interest is set, based on the pixel value of each of a plurality of pixels contained in the region of interest.

In addition, since a convolution sum repetitive operation like that in the related art is not used, the calculation amount is suppressed as compared with the related art.

As has been described above, the medical image processing apparatus 1 according to the first embodiment can generate scattered ray reduced images without excessive correction, while suppressing calculation amounts, from a medical image containing direct radiation and even from a medical image having non-direct radiation components transmitted through a partially thin portion (a small body thickness portion) of the object.

Second Embodiment

FIG. 8 is a block diagram showing an example of the arrangement of an X-ray diagnostic apparatus 25 according to the second embodiment. The X-ray diagnostic apparatus 25 includes an X-ray generation unit 27, an X-ray detection unit 29, a support mechanism 31, a support mechanism driving unit 33, a medical image generation unit 37, an interface unit 3, a storage unit 5, an object thickness decision unit 7, a scattering function decision unit 9, a transformed image generation unit 10, a scattered ray image generation unit 15, a scattered ray reduced image generation unit 17, an input unit 19, a display unit 21, and a control unit 23.

The X-ray generation unit 27 includes an X-ray tube and a high voltage generator (neither of which is shown). The high voltage generator generates a tube current to be supplied to the X-ray tube and a tube voltage to be applied to the X-ray tube. The high voltage generator supplies a tube current suitable for X-ray imaging to the X-ray tube, and applies a tube voltage suitable for X-ray imaging to the X-ray tube. The high voltage generator supplies a tube current suitable for X-ray fluoroscopy to the X-ray tube, and applies a tube voltage suitable for X-ray fluoroscopy to the X-ray tube. The X-ray tube generates X-rays from an X-ray focal point (to be referred to as a tube focal point hereinafter) based on the tube current supplied from the high voltage generator and the tube voltage applied from the high voltage generator.

An X-ray detection unit 29 detects the X-rays generated from the X-ray generation unit 27 and transmitted through an object P. The X-ray generation unit 29 detects the X-rays generated by the X-ray generation unit 27. The X-ray detection unit 29 includes, for example, an FPD (Flat Panel Detector). The FPD includes a photoelectric conversion film which converts light into electrical signals. The FPD converts incident X-rays into electrical signals by using the photoelectric conversion film. The electrical signals generated by the photoelectric conversion film is output to an A/D converter (Analog to Digital converter) (not shown). The A/D converter converts the electrical signals into digital data. The A/D converter outputs the digital data to a preprocessing unit (not shown). The X-ray detection unit 29 has a grid placed in front of the X-ray incident surface. Note that the X-ray detection unit 29 may include an image intensifier.

The preprocessing unit (not shown) executes preprocessing for the digital data output from the X-ray detection unit 29. The preprocessing includes, for example, sensitivity nonuniformity correction between channels in the X-ray detection unit 29 and correction concerning signal omission. The preprocessed digital data is output to a medical image generation unit 37 (to be described later).

A support mechanism 31 movably supports the X-ray generation unit 27 and the X-ray detection unit 29. More specifically, the support mechanism 31 includes, for example, an arm and an arm support portion (neither of which is shown). The arm is, for example, a C-arm. The X-ray generation unit 27 and the X-ray detection unit 29 are mounted on the C-arm so as to face each other. Note that an Ω arm or the like may be used in place of the C-arm. Note that the X-ray diagnostic apparatus 25 may be an X-ray diagnostic apparatus having no arm.

A support mechanism driving unit 33 generates power for driving the support mechanism 31 under the control of the control unit 23. More specifically, the support mechanism driving unit 33 supplies a driving signal corresponding to a control signal from the control unit 23 to the arm support portion to slide and rotate the arm in a predetermined direction. At the time of X-ray imaging or X-ray fluoroscopy, the object P is placed on a top 35 between the X-ray generation unit 27 and the X-ray detection unit 29.

A top driving unit (not shown) generates power for moving the top 35 under the control of the control unit 23.

More specifically, the top driving unit slides the top 35 in the short-axis direction (the X direction in FIG. 8) of the top 35 or the long-axis direction (the Y direction in FIG. 8) of the top 35 based on a control signal from the control unit 23. In addition, the top driving unit generates power for moving the top 35 under the control of the control unit 23. More specifically, the top driving unit generates power for moving the top 35 up and down in the vertical direction (the Z direction in FIG. 8).

The medical image generation unit 37 generates a medical image based on the digital data preprocessed by the preprocessing unit. The medical image generation unit 37 outputs the medical image to the transformed image generation unit 10, the scattered ray reduced image generation unit 17, and the display unit 21, as needed. Note that the medical image generation unit 37 may output the generated medical image to the storage unit 5.

The interface unit 3 may output the medical image acquired from the medical image diagnostic apparatus to the storage unit 5. Note that the interface unit 3 may output the medical image and X-ray conditions acquired from another medical image diagnostic apparatus to the transformed image generation unit 10, the scattered ray reduced image generation unit 17, the display unit 21, and the like, as needed.

The storage unit 5 stores instructions and the like from the operator which are sent from the input unit 19. The storage unit 5 stores the X-ray conditions and the like input by the operator or the like via the input unit 19. Note that the storage unit 5 may store the X-ray conditions acquired from the interface unit 3. Note that the storage unit 5 may store the medical image acquired from the medical image generation unit 37. The storage unit 5 may store the medical image acquired from the interface unit 3. The storage unit 5 may store a program associated with scattered ray correction processing (to be described later).

The object thickness decision unit 7 decides an object thickness based on the X-ray conditions stored in the storage unit 5. The object thickness decision unit 7 includes a memory (not shown) and stores a tube voltage/object thickness correspondence table. More specifically, the object thickness decision unit 7 decides an object thickness based on the X-ray conditions and tube voltage/object thickness correspondence table read out from the storage unit 5.

The scattering function decision unit 9 decides a scattering function based on the X-ray conditions stored in the storage unit 5 and the object thickness decided by the object thickness decision unit 7. The scattering function decision unit 9 includes a memory (not shown) and stores a scattering function correspondence table. More specifically, the scattering function decision unit 9 decides a scattering function based on the object thickness decided by the object thickness decision unit 7, the X-ray conditions read out from the storage unit 5, and the scattering function correspondence table.

The transformed image generation unit 10 generates a transformed image by transforming pixel values, of a plurality of pixel values constituting a medical image, which are higher than the reference value obtained based on the representative value of a plurality of pixel values into pixel values lower than the reference value. The transformed image generation unit 10 includes a reference value decision unit 11 and a pixel value transformation unit 13.

The reference value decision unit 11 decides a reference value based on the representative value of a plurality of pixel values constituting a medical image. More specifically, the reference value decision unit 11 decides a reference value by multiplying the representative value of the plurality of pixel values constituting the medical image by a predetermined constant.

The pixel value transformation unit 13 includes a memory (not shown) and stores a pixel value transformation table. The pixel value transformation unit 13 transforms pixel values, of a plurality of pixel values constituting a medical image, which are higher than a reference value into pixel values lower than the reference value, based on the pixel value transformation table and the reference value. For example, the pixel value transformation unit 13 transforms the pixel values of pixels having direct radiation components in a medical image into low pixel values.

The scattered ray image generation unit 15 generates a scattered ray image based on the transformed image and the scattering function. The scattered ray image is an image obtained by approximately changing the scattering function in accordance with the position of each pixel of the medical image. More specifically, the scattered ray image generation unit 15 generates the Fourier transform of the transformed image. The scattered ray image generation unit 15 generates the Fourier transform of the scattering function. The scattered ray image generation unit 15 divides the Fourier transform of the scattering function by the sum of the Fourier transform of the scattering function and 1 (the division result will be referred to as a scattering function term hereinafter). The scattered ray image generation unit 15 generates the Fourier transform of the scattered ray image by multiplying the Fourier transform of the transformed image by the scattering function term.

The scattered ray reduced image generation unit 17 generates a scattered ray reduced image by subtracting the scattered ray image decided by the scattered ray image generation unit 15 from the medical image. The scattered ray image generation unit 15 outputs the scattered ray reduced image to the display unit 21.

The input unit 19 inputs various types of instructions, commands, information, selections, settings, and the like from the operator and the like to the control unit 23. More specifically, the input unit 19 inputs, to the control unit 23, X-ray conditions, X-ray imaging position, X-ray fluoroscopy position, the start and end of X-ray imaging or X-ray fluoroscopy, an instruction to switch between the display of a projection image and the display of a plurality of tomographic images, and the like as desired by the operator. Note that the input unit 19 may input a predetermined constant to the control unit 23 in accordance with an instruction from the operator. Based on this input, the control unit 23 updates a predetermined constant stored in the memory of the reference value decision unit 11.

The input unit 19 includes input devices such as a trackball, switch buttons, mouse, mouse wheel, and keyboard for inputting various types of instructions, commands, information, selections, settings, and the like. Note that the input device may be a touch panel covering the display screen of the display unit 21. The input unit 19 can input a region of interest on a medical image which is used by the reference value decision unit 11. For example, the operator sets a region of interest by, for example, clicking and dragging the cursor of the mouse on the medical image displayed on the display unit 21.

The display unit 21 displays the scattered ray reduced image generated by the scattered ray reduced image generation unit 17. The display unit 21 can also display a medical image.

The control unit 23 includes a CPU and a memory (neither of which is shown). The control unit 23 temporarily stores, in a memory, information such as an instruction from the operator which is sent from the input unit 19. The control unit 23 comprehensively controls the X-ray generation unit 27, the scattering function decision unit 9, the transformed image generation unit 10, the scattered ray image generation unit 15, and the scattered ray reduced image generation unit 17 to execute X-ray diagnosis in accordance with instructions from the operator which are stored in the memory.

FIG. 9 is a flowchart showing an example of a procedure for scattered ray correction processing according to the second embodiment.

X-ray conditions are input via the input unit 19 (step Sc1). An object thickness is decided based on the input X-ray conditions (step Sc2). A scattering function is decided based on the decided object thickness and the X-ray conditions input in step Sc1 (step Sc3). A reference value is decided based on the representative value of a plurality of pixel values constituting the medical image obtained by X-ray imaging or X-ray fluoroscopy under the readout X-ray conditions (step Sc4). Pixel values, of a plurality of pixel values constituting a medical image, which are higher than the reference value are transformed into pixel values lower than the reference value (step Sc5). A scattered ray image is generated based on the transformed image obtained by transforming the pixel values of the medical image and the scattering function (step Sc6). A scattered ray reduced image is generated by subtracting the scattered ray image from the medical image (step Sc7). The scattered ray reduced image is displayed (step Sc8).

(Modification)

A difference from the second embodiment is that the processing described below is executed. A medical image associated with the first imaging operation (to be referred to as the first medical image hereinafter) is generated by imaging (to be referred to as the first imaging operation hereinafter) an object before X-ray fluoroscopy or X-ray imaging. In addition, a reference value is decided based on the first medical image. Furthermore, based on the decided reference value, scattered ray correction processing is executed for the medical image (to be referred to as the second medical image hereinafter) generated by X-ray fluoroscopy or continuous X-ray imaging (to be referred to as the second imaging operation hereinafter).

The X-ray generation unit 27 generates X-rays from the tube focal point in the first imaging operation. The X-ray generation unit 27 generates X-rays from the tube focal point in the second imaging operation.

The X-ray detection unit 29 detects the X-rays generated from the X-ray generation unit 27 and transmitted through the object in the first imaging operation. The X-ray detection unit 29 detects the X-rays generated from the X-ray generation unit 27 and transmitted through the object in the second imaging operation.

The preprocessing unit (not shown) executes preprocessing for the digital data (to be referred to as the first digital data hereinafter) output from the X-ray detection unit 29 by the first imaging operation. The preprocessed first digital data is output to the medical image generation unit 37. The preprocessing unit executes preprocessing for the digital data (to be referred to as the second digital data hereinafter) output from the X-ray detection unit 29 by the second imaging operation. The preprocessed second digital data is output to the medical image generation unit 37.

The medical image generation unit 37 generates the first medical image based on the preprocessed first digital data. The medical image generation unit 37 outputs the first medical image to the reference value decision unit 11. The medical image generation unit 37 generates the second medical image based on the second digital data generated by the second imaging operation. The medical image generation unit 37 outputs the second medical image to the pixel value transformation unit 13 and the scattered ray reduced image generation unit 17. Note that the first and second medical images may be stored in the storage unit 5.

The transformed image generation unit 10 generates a transformed image by transforming pixel values, of a plurality of pixel values constituting the medical image, which are higher than the reference value obtained based on the representative value of the plurality of pixel values into pixel values lower than the reference value. The transformed image generation unit 10 includes the reference value decision unit 11 and the pixel value transformation unit 13.

The reference value decision unit 11 decides a reference value based on the representative value of the plurality of pixel values constituting the medical image. More specifically, the reference value decision unit 11 decides a reference value by multiplying the representative value of the plurality of pixel values constituting the medical image by a predetermined constant.

The pixel value transformation unit 13 includes a memory (not shown) and stores a pixel value transformation table. The pixel value transformation unit 13 transforms pixel values, of the pixel values constituting the second medical image, which are higher than the reference value into pixel values lower than the reference value, based on the pixel value transformation table and the reference value. The pixel value transformation unit 13 transforms the pixel values of the second medical image generated by the medical image generation unit 37 based on the pixel value transformation table and the reference value.

The scattered ray image generation unit 15 generates a scattered ray image based on the transformed image and the scattering function. The scattered ray image is the image obtained by approximately changing the scattering function in accordance with the position of each pixel of the medical image. More specifically, first of all, the scattered ray image generation unit 15 generates the Fourier transform of the transformed image. The scattered ray image generation unit 15 generates the Fourier transform of the scattering function. The scattered ray image generation unit 15 divides the Fourier transform of the scattering function by the sum of the Fourier transform of the scattering function and 1 (scattering function term). The scattered ray image generation unit 15 generates the Fourier transform of the scattered ray image by multiplying the Fourier transform of the transformed image by the scattering function term. The scattered ray image generation unit 15 generates a scattered ray image by applying an inverse Fourier transform to the Fourier transform of the scattered ray image.

The scattered ray reduced image generation unit 17 generates a scattered ray reduced image by subtracting the scattered ray image from the second medical image generated by the medical image generation unit 37. The scattered ray reduced image generation unit 17 outputs the scattered ray reduced image to the display unit 21.

The display unit 21 displays the scattered ray reduced image generated by the scattered ray reduced image generation unit 17.

Note that in X-ray fluoroscopy or continuous imaging, the X-ray generation unit 27, the X-ray detection unit 29, the preprocessing unit, the medical image generation unit 37, the transformed image generation unit 10, the scattered ray image generation unit 15, the scattered ray reduced image generation unit 17, and the display unit 21 execute processing a plurality of times.

Figure 10:
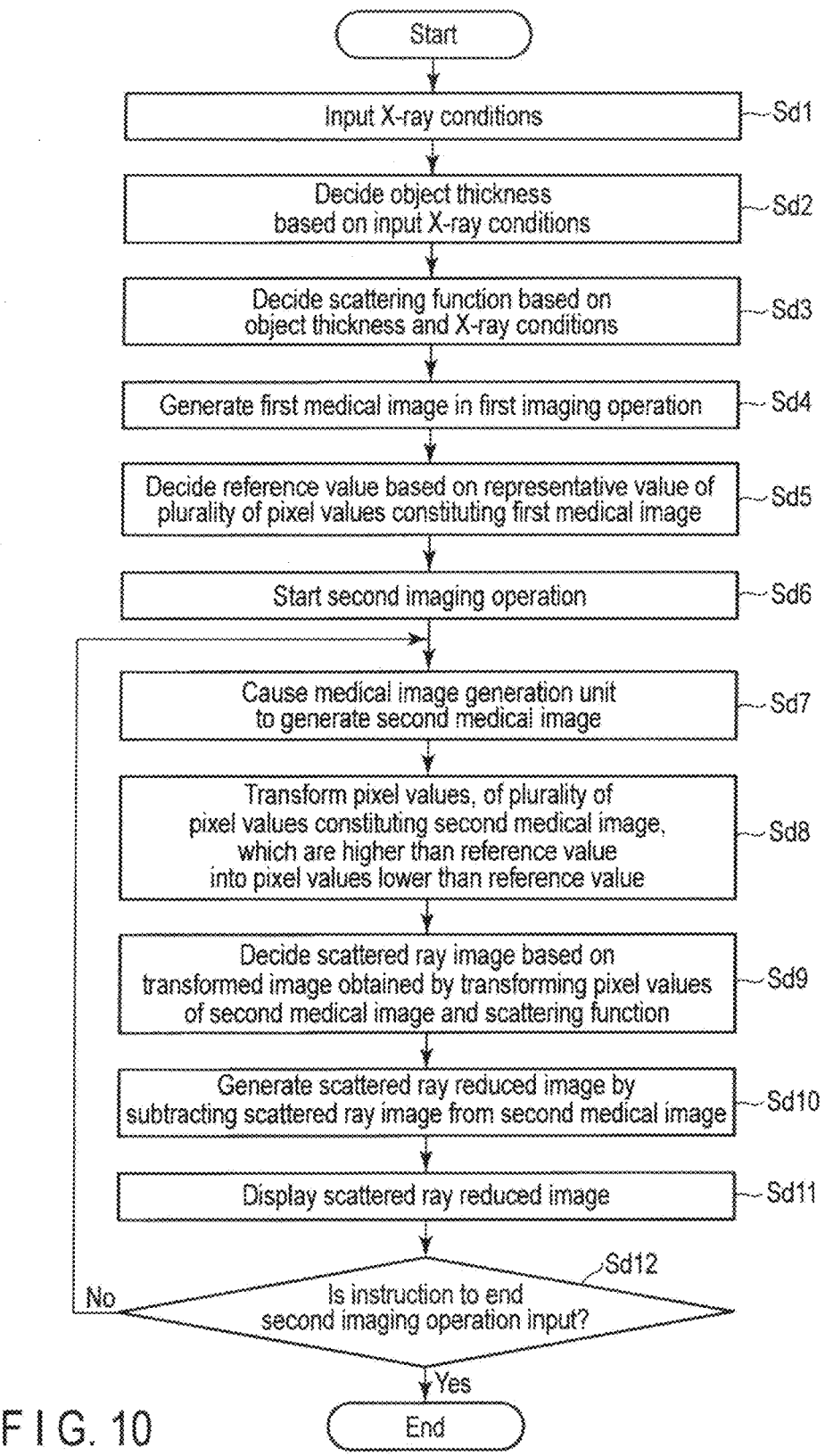
FIG. 10 is a flowchart showing an example of a procedure for scattered ray correction processing according to a modification of the second embodiment.

FIG. 10 is a flowchart showing an example of a procedure for scattered ray correction processing according to the second embodiment.

X-ray conditions are input via the input unit 19 (step Sd1). An object thickness is decided based on the input X-ray conditions (step Sd2). A scattering function is decided based on the decided object thickness and the X-ray conditions input in step Sd1 (step Sd3). The first medical image is generated by the first imaging operation (step Sd4). A reference value is decided based on the representative value of the plurality of pixel values constituting the first medical image (step Sd5). The second imaging operation starts (step Sd6). The medical image generation unit 37 generates the second medical image (step Sd7). Pixel values, of a plurality of pixel values constituting the second medical image, which are higher than the reference value are transformed into pixel values lower than the reference value (step Sd8). A scattered ray image is generated based on the transformed image obtained by transforming the pixel values of the second medical image and the scattering function (step Sd9). A scattered ray reduced image is generated by subtracting the scattered ray image from the second medical image (step Sd10). The scattered ray reduced image is displayed (step Sd11). If an instruction to end the second imaging operation is input, the processing is ended, whereas the instruction is not input, the process returns to step Sd7 (step Sd12).

According to the above arrangement, the following effects can be obtained.

The X-ray diagnostic apparatus 25 according to the second embodiment can decide a reference value based on a medical image. It is possible to generate a transformed image by transforming the pixel value of each of a plurality of pixels constituting the medical image based on the pixel value transformation table and the reference value. The transformed image is obtained by transforming pixel values, of the plurality of pixel values constituting the medical image, which are higher than the reference value into pixel values lower than the reference value. In addition, it is possible to decide a scattering function based on X-ray conditions and an object thickness. According to the embodiment, it is possible to generate a scattered ray image by changing a scattering function in accordance with the position of each pixel of the medical image by using the transformed image. With this operation, a scattered ray image is generated by reducing direct radiation components in the medical image. That is, it is possible to generate a scattered ray reduced image without excessive correction by applying scattered ray correction processing in this embodiment to a medical image having direct radiation components.

The same effects as those with respect to direct radiation components are provided with respect to non-direct radiation components transmitted through a small body thickness portion. A transformed image is obtained by transforming pixel values, of a plurality of pixel values constituting a medical image, which are higher than the reference value into pixel values lower than the reference value. Therefore, the scattered ray image generated based on the above transformed image and the scattering function is the one generated by reducing non-direct radiation components transmitted through a small body thickness portion of the medical image. That is, it is possible to generate a scattered ray reduced image without excessive correction by applying scattered ray correction processing in this embodiment to a medical image having a small body thickness portion.

In addition, according to the modification of the second embodiment, a reference value can be decided in X-ray fluoroscopy or continuous X-ray imaging based on the first medical image obtained before X-ray fluoroscopy or continuous X-ray imaging. It is possible to generate a transformed image by transforming the pixel value of each of the plurality of pixels constituting the second medical image. The transformed image is the one obtained by transforming pixel values, of the plurality of pixel values constituting the second medical image, which are higher than the reference value into pixel values lower than the reference value. A scattering function can be decided based on X-ray conditions and an object thickness. A scattered ray image can be generated based on the transformed image and the scattering function. The scattered ray image is generated by reducing direct radiation components in the second medical image. It is therefore possible to generate a scattered ray reduced image without excessive correction even from the second medical image having direct radiation components.

The same effects as those with respect to direct radiation components are provided with respect to non-direct radiation components transmitted through a small body thickness portion. A transformed image is obtained by transforming pixel values, of a plurality of pixel values constituting the second medical image, which are higher than the reference value into pixel values lower than the reference value. Therefore, the scattered ray image generated based on the above transformed image and the scattering function is the one generated by reducing non-direct radiation components transmitted through a small body thickness portion of the second medical image. It is therefore possible to generate a scattered ray reduced image without excessive correction from the second medical image having non-direct radiation components transmitted through a small body thickness portion.

In addition, since a convolution sum repetitive operation like that in the related art is not used, the calculation amount is suppressed as compared with the related art. In addition, since the number of times of generation of a scattered ray image is reduced as compared with the first embodiment, the calculation amount is further suppressed as compared with the first embodiment.

As has been described above, the X-ray diagnostic apparatus 25 according to the second embodiment can generate scattered ray reduced images without excessive correction, while suppressing calculation amounts, from a medical image having direct radiation components and even from a medical image having non-direct radiation components transmitted through a partially thin portion (a small body thickness portion) of the object.

Third Embodiment

Figure 11:
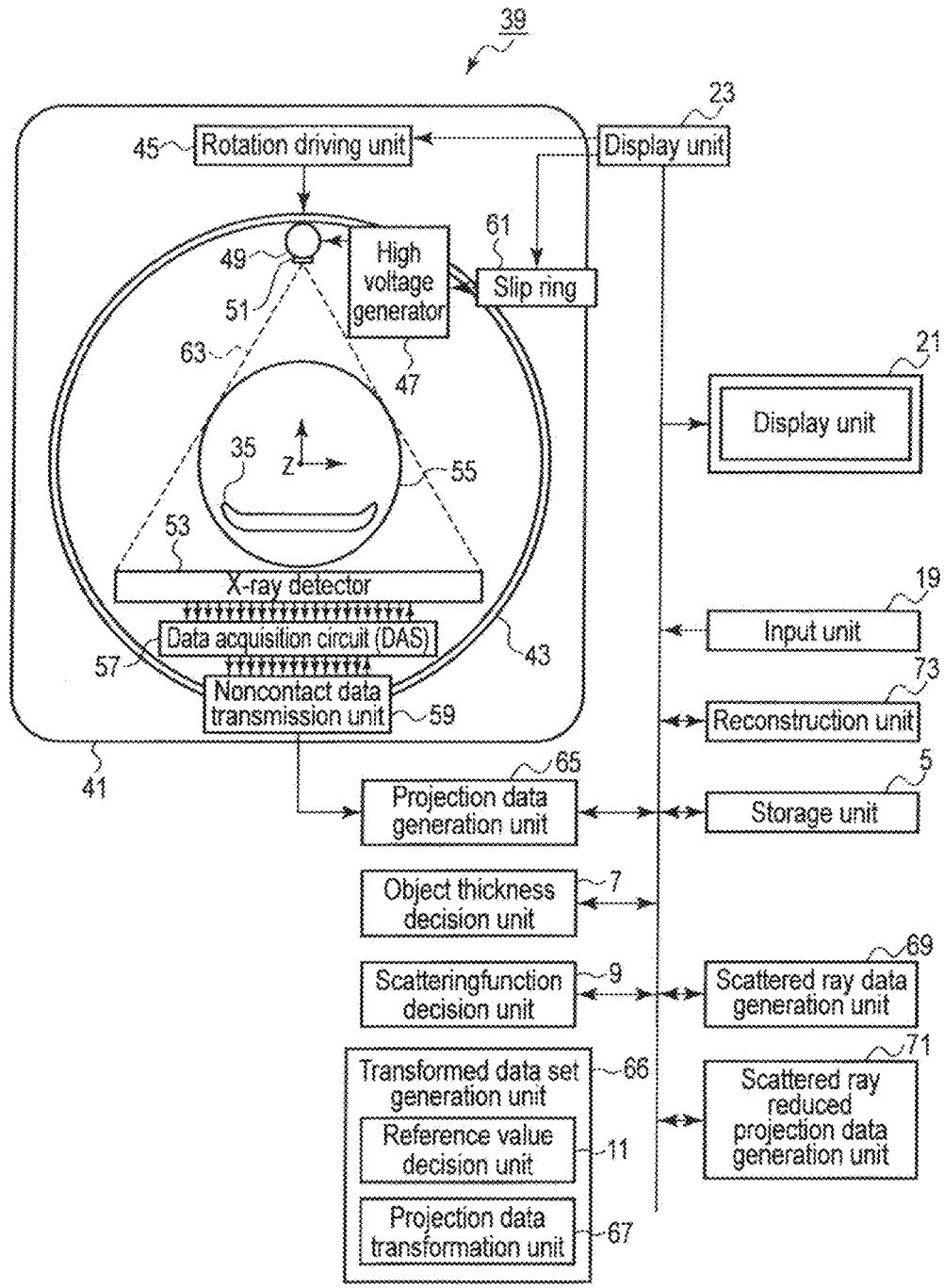
FIG. 11 is a view showing an example of the arrangement of an X-ray computed tomography apparatus according to the third embodiment.

FIG. 11 is a block diagram showing an example of the arrangement of an X-ray computed tomography apparatus 39 according to the third embodiment. The X-ray computed tomography apparatus 39 includes a gantry 41, a projection data generation unit 65, a storage unit 5, an object thickness decision unit 7, a scattering function decision unit 9, a transformed image generation unit 10, a scattered ray data generation unit 69, a scattered ray reduced projection data generation unit 71, a reconstruction unit 73, an input unit 19, a display unit 21, and a control unit 23.

A rotating support mechanism 43 is housed in the gantry 41. The rotating support mechanism 43 includes a rotating ring (not shown), a ring support mechanism (not shown) which supports the rotating ring so as to make it rotatable about the rotation axis Z, and a rotation driving unit 45 which generates power to rotate the rotating ring. The rotating support mechanism 43 is provided with a high voltage generator 47, an X-ray tube 49, a collimator unit 51, an X-ray detector 53 called a two-dimensional array type or multi-array type detector, a DAS (Data Acquisition System) 57, a noncontact data transmission unit 59, a cooling device (not shown), and a gantry controller (not shown). The rotation driving unit 45 is implemented by, for example, a motor.

The high voltage generator 47 generates a high voltage to be applied to the X-ray tube 49 based on power supplied via a slip ring 61. The high voltage generator 47 applies the generated high voltage to the X-ray tube 49. The high voltage generator 47 generates a filament current to be supplied to the X-ray tube 49 based on power supplied via the slip ring 61. The high voltage generator 47 supplies the generated filament current to the X-ray tube 49.

Upon receiving a tube voltage and a tube current from the high voltage generator 47, the X-ray tube 49 radiates X-rays from the X-ray focal point.

The collimator unit 51 mounted on the X-ray radiation window of the X-ray tube 49 shapes the X-rays radiated from the X-ray focal into, for example, a cone beam shape (pyramidal shape). An X-ray radiation range 63 is indicated by the dotted line. The X-axis is a straight line which is perpendicular to the rotation axis Z and passes through the focal point of radiated X-rays. The Y-axis is a straight line perpendicular to the X-axis and the rotation axis Z. For the sake of descriptive convenience, the following description will be made on the assumption that the XYZ coordinate system is a rotating coordinate system which rotates about the rotation axis Z.

The X-ray detector 53 is mounted on the rotating ring at a position and an angle so as to face the X-ray tube 49 through the rotation axis Z. The X-ray detector 53 includes a plurality of X-ray detection elements. In this case, one channel has one X-ray detection element. The X-ray detector 53 has a plurality of channels. The plurality of channels are arranged in a two-dimensional pattern. The two-dimensional pattern is defined by two directions, namely the arc direction (channel direction) and the Z direction (slice direction). In this case, the channel direction is a direction indicated by an arc which is centered on the Z-axis, perpendicular to Z-axis, and has, as its radius, the distance from the X-ray focal point to the light-receiving unit center of an X-ray detection element. Note that the X-ray detector 53 may be formed from a plurality of modules each having one array of a plurality of X-ray detection elements. In this case, the plurality of modules are arrayed in the channel direction.

When performing imaging or scanning, an object is placed on the top 35 and inserted into a cylindrical imaging region 55 between the X-ray tube 49 and the X-ray detector 53. The DAS 57 is connected to the output side of the X-ray detector 53.

The DAS 57 is provided with, for each channel, an I-V converter which converts a current signal from each channel of the X-ray detector 53 into a voltage, an integrator which periodically integrates the voltage signals in synchronism with an X-ray irradiation period, an amplifier which amplifies an output signal from the integrator, and an analog/digital converter which converts an output signal from the amplifier into a digital signal. The data (pure raw data) output from the data DAS 57 is transmitted to projection data generation unit 65 via the noncontact data transmission unit 59 using magnetic transmission/reception or optical transmission/reception.

The projection data generation unit 65 preprocesses the pure raw data output from the DAS 57 to generate projection data (raw data). The preprocessing includes, for example, sensitivity nonuniformity correction processing between channels and the processing of correcting an extreme decrease in signal intensity or signal omission due to an X-ray absorber, mainly a metal portion. The projection data generation unit 65 outputs projection data and data representing view angles associated with each other to the storage unit 5 including a magnetic disk, magneto-optical disk, or semiconductor memory.

Note that projection data is a set of data values corresponding to the intensities of X-rays detected by the X-ray detector 53. For the sake of descriptive convenience, assume that a set of projection data acquired nearly at the same time and at the same view angle throughout all the channels will be referred to as a projection data set. The view angles are represented by angles in the range of 0° to 360° which represent the respective positions on a circular orbit centered on the rotation axis Z, along which the X-ray tube 49 revolves, with the angle of the uppermost portion on the circular orbit in an upward vertical direction from the rotation axis Z being 0°. In this case, −90° and 270° at the same position on the circular orbit represent the same view angle, and 450° and 90° at the same position on the circular orbit represent the same view angle. That is, n° and (n±360°) represent the same view angle. Note that projection data of a projection data set which corresponds to each channel is identified by a view angle, cone angle, and channel number.

The storage unit 5 stores various types of projection data sets and various type of images. The storage unit 5 stores instructions and the like from the operator which are sent from the input unit 19. The storage unit 5 stores the X-ray conditions acquired from the interface unit 3. Note that the storage unit 5 may store a predetermined threshold.

The object thickness decision unit 7 decides an object thickness in each view based on a projection data set corresponding to a view (to be referred to as an object thickness decision view hereinafter), of the views generated from the projection data generation unit 65, which differs by 90° from each view.

Figure 12:
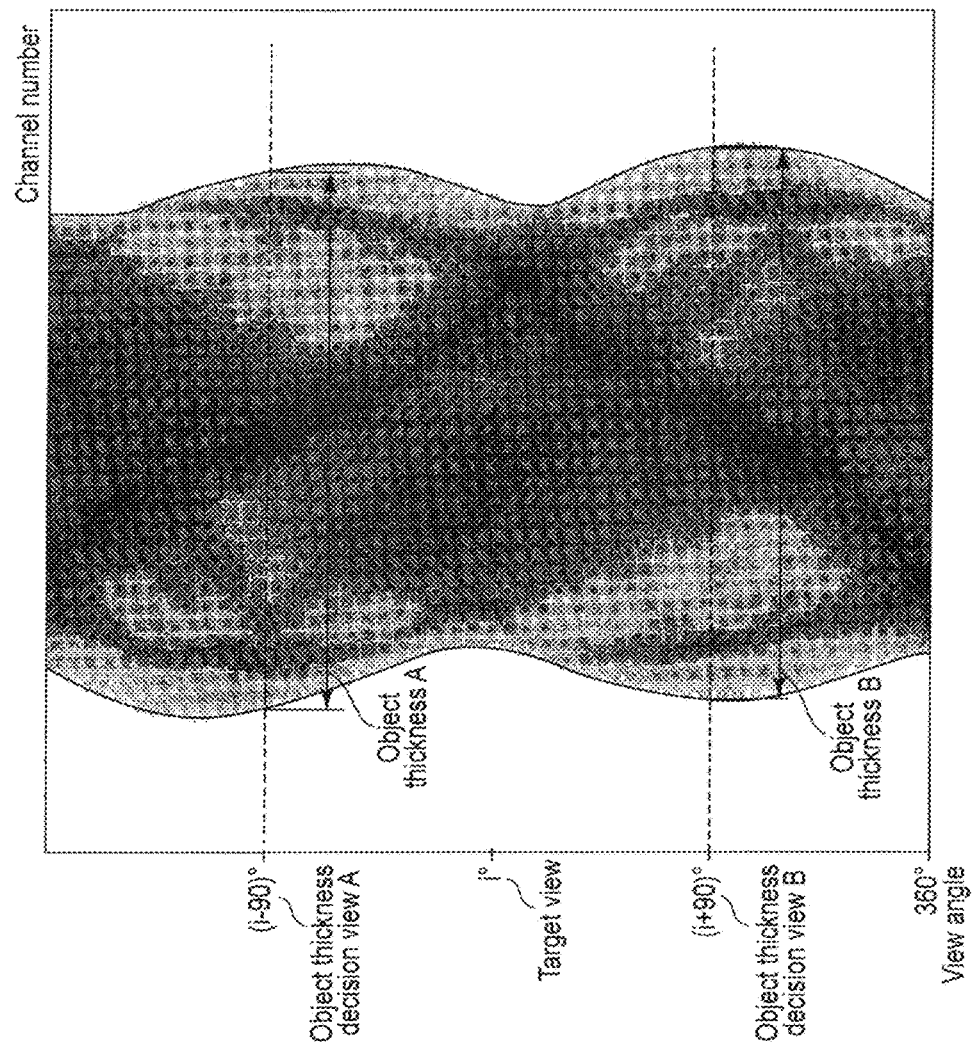
FIG. 12 is a view showing an example of a sinogram representing projection data values defined by view angles and channel numbers by shading according to the third embodiment.

FIG. 12 is a view showing an example of a sinogram representing projection data values defined by view angles and channel numbers by shading. FIG. 12 shows that an object thickness at a view angle i° is decided by using a projection data set corresponding to a view angle of (i−90°) or a projection data set corresponding to a view angle of (i+90°), which differs 90° from the view angle i°. The object thickness decision unit 7 decides an object thickness A or B indicated by the bidirectional arrow in FIG. 12 as an object thickness. More specifically, for example, the object thickness decision unit 7 decides an object thickness based on the interval between channels, of a plurality of channels having projection data values larger than a predetermined threshold, which correspond to the minimum and maximum channel numbers in a projection data set corresponding to a view differing by 90° from the target view. More specifically, the object thickness decision unit 7 decides an object thickness by dividing the actual distance from the minimum channel number to the maximum channel number described above by an enlargement ratio. An enlargement ratio is decided based on the distance between the tube focal point and the object and the distance between the tube focal point and the central point of the detection surface of the X-ray detector 53. Note that the object thickness decision unit 7 may decide an object thickness based on the average value or the like of the object thicknesses A and B.

Note that if no object thickness decision view corresponding to a target view exists, the object thickness decision unit 7 causes the projection data generation unit 65 to generate a projection data set corresponding to an object thickness decision view by using an interpolation method or the like. The projection data generation unit 65 outputs a projection data set corresponding to the generated object thickness decision view to the object thickness decision unit 7. The object thickness decision unit 7 decides an object thickness based on the projection data set corresponding to the object thickness decision view.

The scattering function decision unit 9 decides a scattering function in each view based on the object thickness decided by the object thickness decision unit 7 and the X-ray conditions stored in the storage unit 5. The scattering function decision unit 9 includes a memory (not shown) and stores scattering function correspondence table. More specifically, the scattering function decision unit 9 decides a scattering function in each view based on the object thickness in each view decided by the object thickness decision unit 7 and X-ray conditions and the scattering function correspondence table read out from the storage unit 5.

A transformed data set generation unit 66 generates a transformed data set by transforming projection data values higher than the reference value obtained based on the representative value of a plurality of projection data values constituting each projection data set into projection data values lower than the reference value. The transformed data set generation unit 66 includes the reference value decision unit 11 and a projection data transformation unit 67.

The reference value decision unit 11 decides a reference value for each view based on the representative value of a plurality of projection data values constituting each projection data set. More specifically, the reference value decision unit 11 decides a reference value by multiplying the representative value of a plurality of projection data values constituting each projection data set by a predetermined constant. The reference value decision unit 11 includes a memory (not shown) and stores the predetermined constant.

The projection data transformation unit 67 includes a memory (not shown) and stores a projection data value transformation table. The projection data value transformation table indicates the correspondence relationship between projection data value before transformation and projection data value after transformation. The projection data transformation unit 67 transforms projection data values, of a plurality of projection data values constituting a projection data set, which are higher than the reference values into projection data values lower than the reference value based on the projection data value transformation table and the reference value for each view. For example, the projection data transformation unit 67 transforms projection data values having direct radiation components in a projection data set into lower projection data values.

The scattered ray data generation unit 69 transforms a transformed data set into a scattered ray data set based on the scattering function in each view. More specifically, the scattered ray data generation unit 69 generates the Fourier transform of a transformed data set for each view. The scattered ray data generation unit 69 generates the Fourier transform of a scattering function for each view. The scattered ray data generation unit 69 divides the Fourier transform of a scattering function for each view by the sum of the Fourier transform of the scattering function for each view and 1 (scattering function term). The scattered ray data generation unit 69 generates the Fourier transform of a scattered ray data set for each view by multiplying the Fourier transform of a transformed data set for each view by the scattering function term for each view. The scattered ray data generation unit 69 generates a scattered ray data set in each view by applying an inverse Fourier transform to the Fourier transform of a scattered ray data set for each view. Note that scattered ray data sets are generated by the number of views.

The scattered ray reduced projection data generation unit 71 generates a scattered ray reduced projection data set with reduced scattered rays by subtracting a scattered ray data set from a projection data in each view. Note that scattered ray reduced projection data sets are generated by the number of views. The scattered ray reduced projection data generation unit 71 outputs scattered ray reduced projection data sets to the display unit 21.

The reconstruction unit 73 reconstructs volume data based on scattered ray reduced projection data sets at view angles in the range of 360° or (180+fan angle)°. The volume data is stored in the storage unit 5.

The input unit 19 inputs various types of instructions, commands, information, selections, settings, and the like from the operator or the like to the control unit 23. Note that the input unit 19 may input a predetermined constant to the control unit 23 in accordance with an instruction from the operator. Based on the input, the control unit 23 updates the predetermined constant stored in the memory of the reference value decision unit 11.

The input unit 19 includes input devices such as a trackball, switch buttons, mouse, mouse wheel, and keyboard for inputting the above various types of instructions, commands, information, selections, settings, and the like. Note that the input device may be a touch panel covering the display screen of the display unit 21.

The display unit 21 displays the scattered ray reduced projection data set generated by the scattered ray reduced projection data generation unit 71.

The control unit 23 includes a CPU and a memory (neither of which is shown). The control unit 23 temporarily stores, in a memory, information such as an instruction from the operator which is sent from the input unit 19. The control unit 23 comprehensively controls the object thickness decision unit 7, the scattering function decision unit 9, the transformed image generation unit 10, the scattered ray data generation unit 69, the scattered ray reduced projection data generation unit 71, and the like to execute image processing in accordance with instructions from the operator which are stored in the memory.

Figure 13:
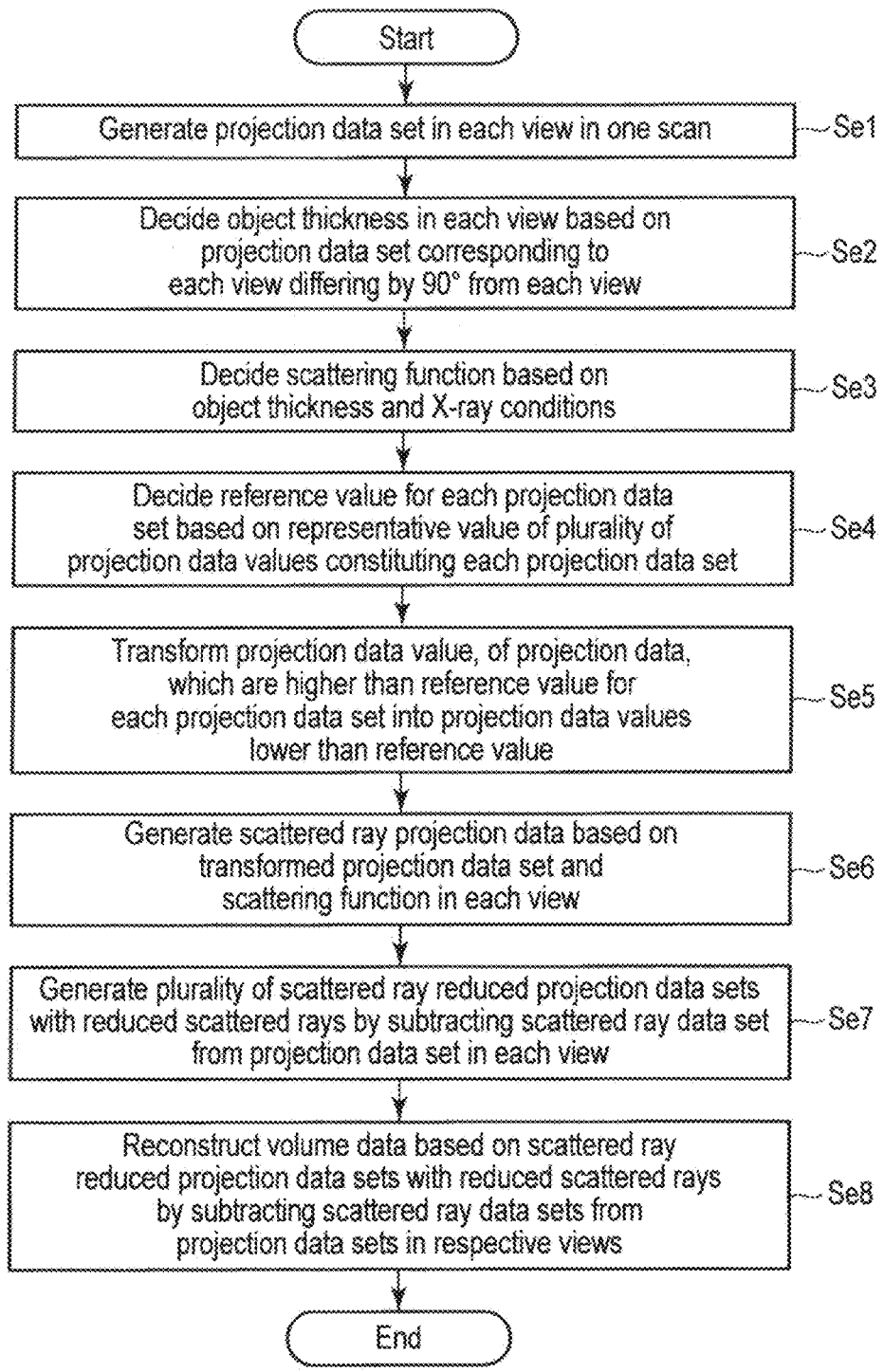
FIG. 13 is a flowchart showing an example of a procedure for scattered ray correction processing according to the third embodiment.

FIG. 13 is a flowchart showing an example of a procedure for scattered ray correction processing according to the third embodiment.

A projection data set for each view in one scan is generated (step Se1). An object thickness in each view is decided based on a projection data set in a view which differs by 90° from each view (step Se2). A scattering function is decided based on the decided object thickness and the X-ray conditions stored in advance in the storage unit 5 (step Se3). A reference value for each projection data set is decided based on the representative value of a plurality of projection data values constituting each projection data set (step Se4). Projection data values, of the projection data values, which are higher than the reference value for each projection data set are transformed into projection data values lower than the reference value (step Se5). A scattered ray projection data set is generated based on the transformed projection data set and the scattering function in each view (step Se6). A plurality of scattered ray reduced projection data sets with reduced scattered rays are generated by subtracting the scattered ray data sets from the projection data sets in the respective views (step Se7). Volume data is reconstructed based on the generated scattered ray reduced projection data sets in the plurality of views (step Se8).

According to the above arrangement, the following effects can be obtained.

The X-ray computed tomography apparatus 39 according to the third embodiment decides an object thickness in each view based on a projection data set corresponding to a view which differs by 90° from each view. A scattering function can be decided based on an object thickness and X-ray conditions. A reference value for each projection data set can be decided based on the representative value of a plurality of projection data values constituting each projection data set. A transformed projection data set can be generated by transforming a plurality of projection data values by using a reference value corresponding to each projection data set. A transformed projection data set is the one obtained by transforming projection data values, of a plurality of projection data values constituting a projection data set, which are higher than the reference value into projection data values lower than the reference value. According to this embodiment, it is possible to generate a scattered ray data set by changing a scattering function in accordance with a data number of a projection data set. With this operation, a scattered ray data set is generated by reducing direct radiation components in a projection data set. That is, it is possible to generate a scattered ray reduced projection data set without excessive correction by applying scattered ray correction processing in this embodiment to a projection data set having direct radiation components. It is therefore possible to generate volume data having undergone scattered ray reduction processing without excessive correction by reconstructing scattered ray reduced projection data sets.

The same effects as those with respect to direct radiation components are provided with respect to non-direct radiation components transmitted through a small body thickness portion. A transformed projection data set is obtained by transforming projection data values, of a plurality of projection data values constituting a projection data set, which are higher than the reference value into projection data values lower than the reference value. Therefore, the scattered ray data set generated based on the above transformed projection data set and the scattering function is the one generated by reducing non-direct radiation components transmitted through a small body thickness portion in the projection data set. That is, it is therefore possible to generate a scattered ray reduced projection data set without excessive correction by applying scattered ray correction processing in this embodiment to a projection data set having non-direct radiation components transmitted through a small body thickness portion. It is therefore possible to generate volume data having undergone scattered ray reduction processing without excessive correction by reconstructing scattered ray reduced projection data sets.

In addition, each function according to each embodiment can be implemented by installing a scattered ray correction processing program in a computer such as a workstation and expanding it in the memory. In this case, the program which can cause the computer to execute the corresponding technique can be distributed by being stored in storage media such as magnetic disks (floppy disks, hard disks, and the like), optical disks (CD-ROMs, DVDs, and the like), and semiconductor memories.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A medical image processing apparatus comprising:
processing circuitry configured to:
generate a single transformed image by transforming pixel values, of a plurality of pixel values constituting a medical image, which are higher than a reference value corresponding to direct radiation components, which are components of X-rays not transmitted through an object, or non-direct radiation components, which are components of X-rays transmitted through a thin portion of the object, into lower pixel values;
transform the single transformed image into a single scattered ray image based on a scattering function; and
generate a scattered ray reduced image with reduced scattered rays by subtracting the single scattered ray image from the medical image.

2. The apparatus according to claim 1, wherein the processing circuitry is configured to transform pixel values, of the plurality of pixel values, which are higher than the reference value into pixel values lower than the reference value.

3. The apparatus according to claim 1, wherein the processing circuitry is configured to determine the reference value based on a representative value of the plurality of pixel values.

4. The apparatus according to claim 3, wherein the representative value is a mode value of the plurality of pixel values.

5. The apparatus according to claim 4, wherein the representative value is an average value or a median value of a plurality of pixel values contained in a region of interest of the medical image.

6. The apparatus according to claim 1, wherein the processing circuitry is configured to:
determine an object thickness based on an X-ray condition associated with the medical image or projection data; and
determine the scattering function based on the X-ray condition and the object thickness.

7. The apparatus according to claim 1, wherein the processing circuitry is configured to transform a Fourier transform of the single transformed image into the single scattered ray image based on a Fourier transform of the scattering function.

8. An X-ray diagnostic apparatus including the medical image processing apparatus according to claim 1, the X-ray diagnostic apparatus further comprising:
an X-ray tube configured to generate X-rays; and
an X-ray detector configured to detect the X-rays;
wherein the processing circuitry is configured to generate the medical image based on an output from the X-ray detector.

9. The apparatus according to claim 3, wherein the processing circuitry is configured to determine the reference value by multiplying the representative value by a predetermined constant.

\* \* \* \* \*